US008709803B2

(12) United States Patent
Gartzia Aranaga et al.

(10) Patent No.: US 8,709,803 B2
(45) Date of Patent: Apr. 29, 2014

(54) CELL TRANSPORT SYSTEM COMPRISING A HOMOGENEOUS MIXTURE OF AGAROSE AND AGARASE

(75) Inventors: Miren Itxaso Gartzia Aranaga, Derio (ES); Maite Del Olmo Basterrechea, Derio (ES); Maria Begoña Castro Feo, Derio (ES); Marta Acilu Perez, Derio (ES)

(73) Assignee: Histocell, S.L., Derio (ES)

( * ) Notice: Subject to any disclaimer, the term of this patent is extended or adjusted under 35 U.S.C. 154(b) by 305 days.

(21) Appl. No.: 13/140,721

(22) PCT Filed: Dec. 18, 2009

(86) PCT No.: PCT/EP2009/009132
§ 371 (c)(1),
(2), (4) Date: Sep. 8, 2011

(87) PCT Pub. No.: WO2010/069589
PCT Pub. Date: Jun. 24, 2010

(65) Prior Publication Data
US 2012/0135445 A1    May 31, 2012

(30) Foreign Application Priority Data
Dec. 19, 2008   (ES) .................................. 200803631

(51) Int. Cl.
*C12N 5/00* (2006.01)
*C12M 1/00* (2006.01)

(52) U.S. Cl.
USPC ......................... 435/374; 435/397; 435/307.1

(58) Field of Classification Search
None
See application file for complete search history.

(56) References Cited

U.S. PATENT DOCUMENTS 6,184,011 B1    2/2001   Siegel et al.

FOREIGN PATENT DOCUMENTS

| EP | 0 702 081 A2 | 3/1996 |
|---|---|---|
| EP | 1 650 292 A1 | 4/2006 |
| WO | 01/40445 A1 | 6/2001 |
| WO | 2007/080600 A1 | 7/2007 |

OTHER PUBLICATIONS

L. Wang, et al., "Flow cytometric analysis of the human articular chondrocyte phenotype in vitro", Osteoarthritis and Cartilage, 2001, p. 73-84, vol. 9.
L. Wang, et al., "Evaluation of chondrocyte cell-associated matrix metabolism by flow cytometry", Osteoarthritis and Cartilage, 2001, p. 454-462, vol. 9.
Ann B. Zimrin, "An Antisense Oligonucleotide to the Notch Ligand Jagged Enhances Fibroblast Growth Factor-induced Angiogenesis in Vitro", The Journal of Biological Chemistry, Dec. 20, 1996, p. 32499-32502, vol. 271, No. 51.
Matthias Ernst, et al., "gp130-mediated Signal Transduction in Embryonic Stem cells Involves Activation of Jak and Ras/Mitogen-activated Protein Kinase Pathways", The Journal of Biological Chemistry, Nov. 22, 1996, p. 30136-30143, vol. 271, No. 47.
Megan E. Laurance, et al., "Differential Activation of Viral and Cellular Promoters by Human T-cell Lymphotropic Virus-1 Tax and cAMP-responsive Element Modulator Isoforms", The Journal of Biological Chemistry, Jan. 31, 1997, p. 2646-2651, vol. 272, No. 5.
Toshiyuki Yoneda, et al., "Inhibition of Osteolytic Bone Metastasis of Breast Cancer by Combined Treatment with the Bisphosphonate Ibandronate and Tissue Inhibitor of the Matrix Metalloproteinase-2", The American Society for Clinical Investigation, Inc., May 1997, p. 2509-2517, vol. 99, No. 10.
Kathrin H. Kirsch, et al., "CMS: An adapter molecule involved in cytoskeletal rearrangements", Proc. Natl. Acad. Sci. USA, May 1999, p. 6211-6216, vol. 96.
Inga Ivankovic-Dikic, et al., "Pyk2 and FAK regulate neurite outgrowth induced by growth factors and integrins", Nature Cell Biology, Sep. 2000, p. 574-581, vol. 2.
Kristi A. Miller, et al., "Inhibition of Laminin-5 Production in Breast Epithelial Calls by Overexpression of p300", The Journal of Biological Chemistry, Mar. 17, 2000, p. 8176-8182, vol. 275, No. 11.
Phillip S. Leventhal, et al., "Tyrosine Phosphorylation and Enhanced Expression of Paxillin during Neuronal Differentiation in Vitro", The Journal of Biological Chemistry, Mar. 15, 1996, p. 5957-5960, vol. 271, No. 11.
Ali Khademhosseini, et al., Conformal Coating of Mammalian Cells Immobilized onto Magnetically Driven Beads, Tissue Engineering, 2005, p. 1797-1807, vol. 11, No. 11/12.
Kim S. Jones, et al., "In Vivo Recognition by the Host Adaptive Immune System of Microencapsulated Xenogeneic Cells", Transplantation, Nov. 27, 2004, p. 1454-1462, vol. 78, No. 10.
B. Rahfoth, et al., "Transplantation of allograft chondrocytes embedded in agarose gel into cartilage defects of rabbits", Osteoarthritis and Cartilage, 1998, p. 50-65, vol. 6.
Yibo Ling, et al., "A cell-laden microfluidic hydrogel", The Royal Society of Chemistry, 2007, p. 756-762, vol. 7.

(Continued)

*Primary Examiner* — Sandra Saucier
(74) *Attorney, Agent, or Firm* — Sughrue Mion, PLLC

(57) ABSTRACT

The present invention relates to a system for cell transport Said system allows the transport of cells, assuring their integrity and viability during the entire transport process. It consists of a system suitable for a wide variety of formats which allows a broad range of technical applications of the system The system of the invention allows providing ready-to-use cells, without the cells having to be manipulated before they are used by technical experts in cell biology The invention particularly relates to an agarose plus agarase mixture covering or enveloping, depending on the format of the selected transport system, the cell culture, protecting it during the transport process, as well as to the methodology of cell recovery of the cells transported in the system.

48 Claims, 13 Drawing Sheets
(2 of 13 Drawing Sheet(s) Filed in Color)

(56) References Cited

OTHER PUBLICATIONS

A.P. Balgude, et al., "Agarose gel stiffness determines rate of DRG neurite extension in 3D cultures", Biomaterials, 2001, p. 1077-1084, vol. 22.

Po-Wei Lin, et al., "Characterization of Cortical Neuron Outgrowth in Two- and Three-Dimensional Culture Systems", Wiley InterScience, Jul. 6, 2005, p. 146-157.

R.L. Mauck, "Regulation of cartilaginous ECM gene transcription by chondrocytes and MSCs in 3D culture in response to dynamic loading", Biomechan Model Mechanobiol, 2007, p. 113-125, vol. 6.

Benton C Martin, et al., "Agarose and methylcellulose hydrogel blends for nerve regeneration applications", Journal of Neural Engineering, 2008, p. 221-231, vol. 5.

Ying Luo, et al., "Light-Activated Immobilization of Biomolecules to Agarose Hydrogels for Controlled Cellular Response", Biomacromolecules, 2004, p. 2315-2323, vol. 5.

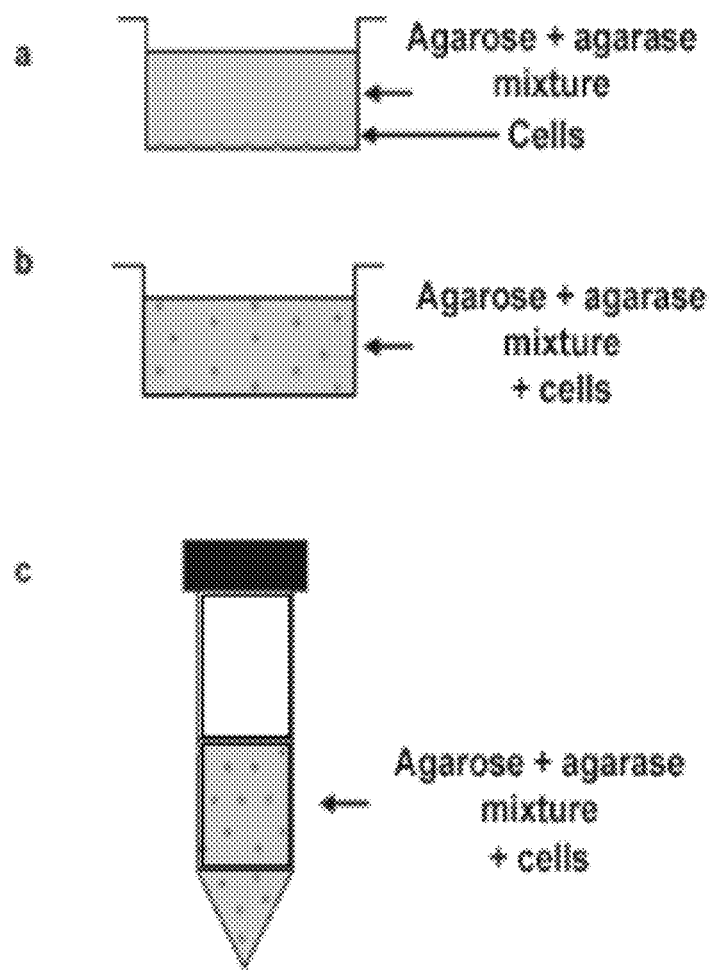

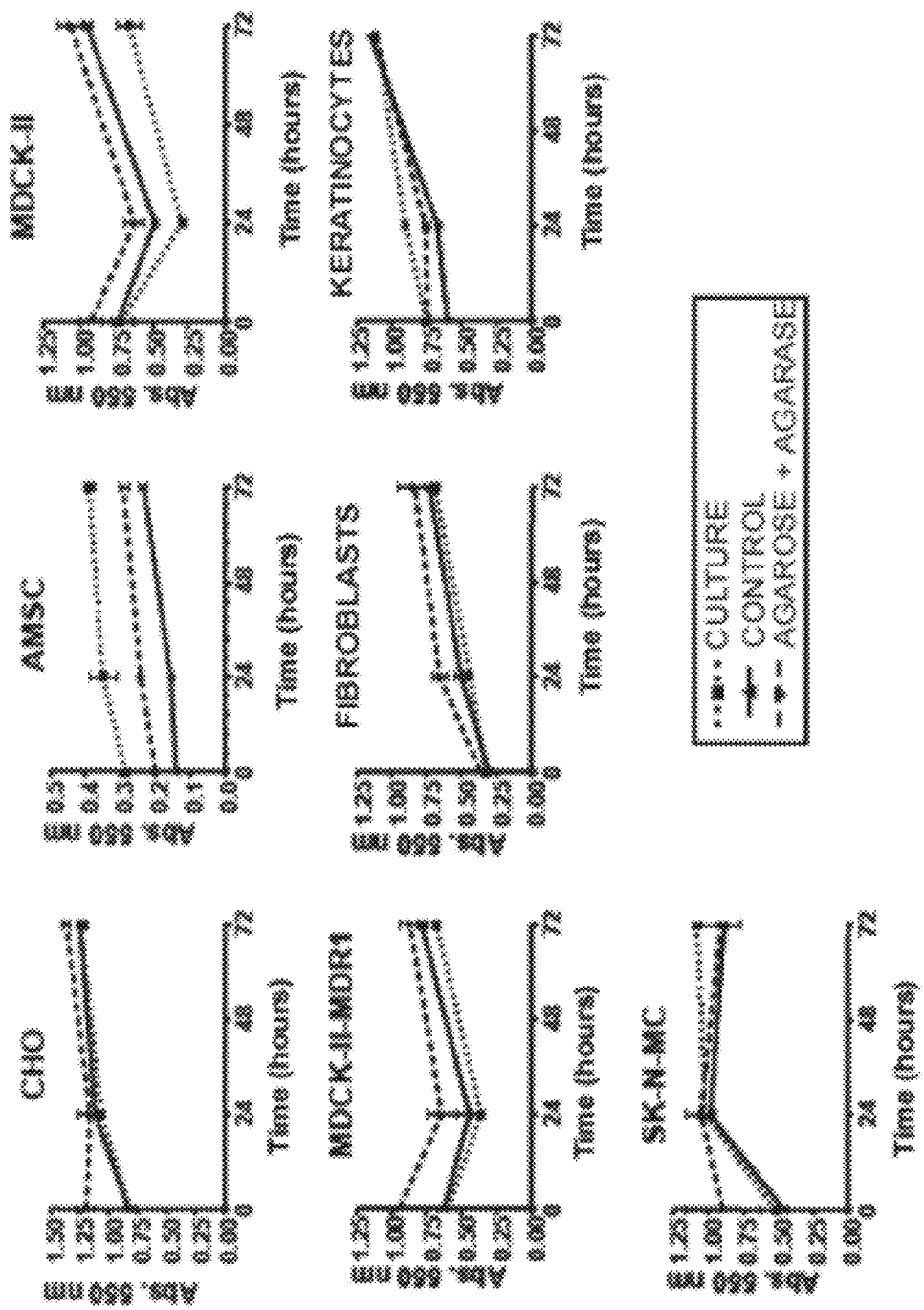

CELL TRANSPORT SYSTEM COMPRISING A HOMOGENEOUS MIXTURE OF AGAROSE AND AGARASE

CROSS REFERENCE TO RELATED APPLICATIONS

This application is a National Stage of International Application No. PCT/EP2009/009132 filed Dec. 18, 2009, claiming priority based on Spain Patent Application No. P200803631 filed Dec. 19, 2008, the contents of all of which are incorporated herein by reference in their entirety.

TECHNICAL FIELD OF THE INVENTION

The present invention relates to a system for cell transport. Said system allows the transport of cells, assuring their integrity and viability during the entire transport process. It consists of a system suitable for a wide variety of formats which allows a broad range of technical applications of the system. The system of the invention allows providing ready-to-use cells, without the cells having to be manipulated before they are used by technical experts in cell biology. The invention particularly relates to an agarose plus agarase mixture covering or enveloping, depending on the format of the selected transport system, the cell culture, protecting it during the transport process, as well as to the methodology of cell recovery of the cells transported in the system.

BACKGROUND OF THE INVENTION

There is an interest in the state of the art to obtain transport systems which, maintaining the integrity and viability of the cells, do not requiring handling complicated methodologies, both during their transport and during the process for the recovery of the cells, in their final destination.

Cell transport is currently carried out in two different ways, which is by transporting cells in a cryopreserved state or in a cultured state.

The techniques for the transport of cells in culture allow the cells to be adhered or in suspension in flasks with liquid culture medium. In this methodology, it is necessary to be extremely careful with the transport conditions because small movements sustained over time during their transport definitively affect the integrity and cell adhesion capacity and therefore the viability of the cells in their destination. This means that most of the cultures thus transported do not reach their place destination in conditions of viability that are suitable for being used in the various research projects, understanding cell viability as there being no morphological and/or functional alterations in the cells.

This is why an effective cell culture transport system must assure that during the entire transport process and the process for the recovery of the cells for their use, the integrity thereof is optimally maintained (references 15-19), i.e., the viability thereof is not affected during the entire process.

Transport in the cryopreserved state involves the transport of vials of cells in a cryofrozen state, which means that in order for the cells to be used again, the place of destination must have installations and personnel that are specialized in cell culture, a tedious manipulation including cell amplification and maintenance, and the arrangement of the cells in the formats required for carrying out the testing techniques, being necessary.

So one aspect to take into account in cell transport is the temperature at which the cells are transported, because this temperature directly affects the maintenance of the cell integrity due to the fact that most cell lines and types are sensitive to temperature changes.

Cryopreservation involves very low and constant transport temperatures that are difficult to maintain the entire transport time. This means that transport must take place in very specific conditions, i.e., the vials must be kept at temperatures of less than −80° C. during the entire transport process because cell viability would otherwise be seriously affected.

The optimal growth temperature for animal cell cultures is 36-38° C. Once this temperature range is exceeded (hyperthermia conditions) cell viability is affected, irreversibly damaging the integrity of the cells of the culture and causing cell death.

Temperatures under the optimal temperature range (hypothermia conditions) are better tolerated by cell cultures than high temperatures are. So, in the case of the application of a temperature of less than the optimal recommended temperature, decreased cell metabolism occurs, i.e., the cell reactions (proliferation, metabolisms, growth, . . . ) slow down but the cell maintains its integrity, and when optimal thermal conditions for growth are restored, the cells recover their cell activity.

In the state of the art, hypothermia is a widely used methodology for slowing down the growth of microorganisms and tumor cells. The system described in the present invention makes use of said characteristic such that the cells have slowed metabolism during transport, aiding in the maintenance of their integrity.

The state of the art comprises several systems for the transport of cells in culture. In certain documents, the cell cultures are covered with culture media at 1-20% of liquid gelatin which, after solidification, can be transported without the cells being damaged. Other documents, however, describe specific devices for the culture, storage and transport of cell cultures.

Patent application P200301526 describes a method for the storage and transport of two-dimensional cell cultures in which the cells are immobilized on a transwell-type asymmetric support which is covered with a gelatin solution at a concentration of 1 to 5% which solidifies by cooling, thus facilitating that the system can be transported, maintaining the cell integrity of the culture. The plate is incubated in the laboratory of destination at 37° C. for 4 hours so that the gelatin liquefies and can be removed from the cell culture, the cells being ready to perform the appropriate migration assays. This system, however, does not allow using the cell culture for applications other than assays in transwell-type asymmetric supports.

In contrast, the invention proposed in the present document is suitable for any cell culture format required according to its specific application either in the transport system itself or once it is extracted therefrom and allows cell recovery to occur in a time of not more than 3 hours, which is less time than that described by Spanish patent application P200301526 (4 hours).

European patent EP0702081 describes a method for the storage and transport of three-dimensional tissues. The invention described in this document consists of placing a three-dimensional culture of skin fixed on two types of sponge covered with a gelatin solution of 1-20%, preferably of 5-10%, such that when the solution gels by cooling, this facilitates its transport and storage. As in the aforementioned Spanish patent application, this document describes the method used to remove the gelatin from the three-dimensional culture which consists of increasing the temperature up to a maximum of 37° C. to liquefy it, preserving the cell integrity of the system. The document specifies that the use of agarose would not be suitable for this system because the melting point of agarose is around 60° C., i.e., much higher than the temperature allowing cell viability. The system described by this document furthermore does not allow the recovery of the cell culture for its use outside same.

International patent application WO2007/080600 describes a disposable device for the culture and/or storage and transport of viable adherent cells. In said device, the cells are seeded on membranes, gels or microporous substrates held to the device on which a medium providing the cells with the nutrients necessary for maintaining their growth will later be added. The device closes securely, preventing losses of liquid and the entrance of air in the compartment in which the cells are cultured. Once the device reaches its destination, the membrane, gel or substrate on which the cells are seeded is extracted and cleaned and it can then be transplanted. However, the document does not indicate in any case that the cells are separate from the membrane on which they are cultured, such that such cells cannot be used independently. The device described by this document furthermore does not allow the transport of cell cultures which are not adherent.

Therefore, the present invention presents as a transport medium an agarose and agarase solution which gels at room temperature and which can be removed once the sample reaches its destination after heating the system to 37° C., as a result of the activation of the agarase at said temperature which facilitates the digestion of agarose. The system furthermore is suitable for any culture format, including plates, culture chambers, bottles, tubes, transwell-type asymmetric supports, etc.

The transport system mentioned in the present invention assures that the cells can be transported in culture, both adhered and in suspension, preventing that the movements derived from transport damage cell integrity and therefore maintaining optimal cell viability that allows recovering the transported cells or carrying out different types of assays with them.

Agarose is a thermally reversible polysaccharide consisting of alternating (1-3) linked β-D-galactose and (1-4) linked (3-6)-anhydrous-α-L-galactose copolymers, and it is commonly used in cell encapsulation. Agarose can be melted or gelled through changes in the temperature to which it is subjected.

Cell encapsulation in agarose is known in the state of the art for carrying out a wide variety of applications, such as for example the use of cells as biosensors, for therapeutic uses, etc. (references 11, 12). In addition, the biocompatibility the agarose has been proven by means of in vivo implantation studies (references 1, 2, 13). It has furthermore been observed that the cells that have been encapsulated in agarose hydrogels have the capacity to secrete their own extracellular matrix (reference 14) which reflects that the functional behavior of the cells is not altered in this medium. However, agarose is not a medium commonly used in forming three-dimensional cultures, since it does not seem to induce cell proliferation in this type of cell culture.

Agarase is an enzyme with a molecular weight of 32 kDA that hydrolyzes the [1-3] linkages between D-galactose and 3,6-anhydrous-L-galactose residues of agarose.

The state of the art also describes how cultures encapsulated with agarose can be recovered by means of treatment with an agarase solution added on the culture. In these cases the receiving laboratory must have agarase, prepare the mixture at the necessary concentration and adding it to the system. However the digestion of agarose following this method is not homogenous because the agarase is not in direct contact with all the agarose gel, which increases the recovery time, finally reducing cell viability.

An example can be found in references 1 and 2, which show the recovery of cell cultures embedded in a 1.5% agarose solution. To carry out said recovery, the three-dimensional structure is treated with an agarase solution that is added independently. Document WO2001/40445 uses a 2% agarose solution to treat a cell or cell populations and to capture the substances said cells secrete. The agarose used is previously treated to incorporate cytokine- and hormone-specific binding sites therein. To remove the agarose matrix, an agarase solution causing the enzymatic digestion of agarose is added.

In contrast, the system of the present invention involves the use of a homogenous agarose-agarase mixture as the transport medium, which prevents the receiving laboratory from having to have agarase, prepare the mixture at the necessary concentration and add it to the system. Furthermore, the system of the present invention favors a homogenous digestion throughout the entire cell culture, achieving optimal viability of the recovered cell cultures.

An additional advantage of the system of the present invention is the fact that it uses lower percentages of agarose, which means that during cell recovery, the amount of agarase necessary for the complete digestion of agarose is lower and therefore the cells will not be affected by its enzymatic action, showing no alterations in terms of the viability and proliferative capacity thereof.

In view of the state of the art, there is obviously a need to provide a standard cell transport system for both adherent and non-adherent cell cultures, suitable for any cell culture format and application of the system, which assures the integrity and viability of the cell culture during the transport process, and that the cell recovery process does not require installations or personnel specialized in cell culture, is obvious. The transport system described in the present invention proposes a simple cell transport system which allows transporting cells in culture, both adhered and in suspension, with maximum quality standards and viability, and furthermore does not necessarily require a specific infrastructure for recovering and using the cell culture if the final application of the transported cells does not require this.

The transport conditions required by the system described by the present invention are not conditions that require a cooled transport temperature, and the transport time is not a risk factor either because the cell transport system of the invention allows the cells to be transported at temperatures of not more than 25° C. during a broad time interval without affecting the viability of the cell culture.

OBJECT OF THE INVENTION

The present invention provides a system for cell transport which allows transporting cells, assuring integrity and viability during the process and is adaptable for a wide variety of formats, covering a broad range of applications of the system.

In said system, the cells are covered with or embedded in a homogenous agarose plus agarase mixture, which once solidified allows cell transport. The system is transported in a temperature range of not more than 25° C., preferably between 18 and 23° C., more preferably at 22° C., such that the agarase remains inactive. Cell recovery is carried out simply by means of incubation of the system at 37° C., which involves activating the agarase, which digests the agarose facilitating its liquefying, and allowing the removal thereof from the culture support prior to use.

The recovered cell cultures maintain their integrity and viability, certifying the effectiveness of the transport system, i.e., the transport system described in the present invention substantially improves the viability of the cell culture in transport conditions.

Thus, this system allows providing ready-to-use cells, the cell recovery process of which requires manipulation and minimal knowledge in cell biology techniques.

In the present invention:

Cell transport relates to transporting cell cultures.

The quality standard means that at least 85%, preferably 100% of the cells transported by the system of the invention, have not been affected in terms of their cell viability and integrity.

Cell viability and integrity relates to the maintenance of the morphological and functional cell properties, such as cell adhesion capacity, and basic cell parameters such as proliferation and metabolic activity.

Consistency of the transport medium relates to the semisolid consistency, once the agarose-agarase mixture has gelled, which prevents the sustained movements occurring during the transport thereof from finally affecting cell viability and integrity and assuring the quality standards defined for the system of the invention as well as an easy recovery of the cell culture.

Transport medium relates to the agarose-agarase mixture used to transport cells in culture. In which the percentage of agarose used is 0.2-0.6%, preferably 0.5%, and the agarase concentration is 60-90, preferably 80 units per ml of 1% agarose.

Cells in culture relates to the cell population in cell culture conditions, applied both to cells in suspension and to those cells that grow adhered, forming a monolayer on surfaces which can have optionally been treated beforehand with components of the extracellular matrix that increase cell adhesion (laminin, collagen, poly-L-lysine, etc.) of certain semi-adherent cell types.

Cell culture relates to any type of monolayer cell culture in three-dimensional (3D) systems or in suspension, including genetically modified cells or not, of any origin preferably animal cells such as: human, murine (mice, rats, hamsters), canine, bovine, ovine, etc. Said cell cultures include nervous cells, cells of the central nervous system, cells of the peripheral nervous system, cells of the dermo-epithelial system, cells of the osteoarticular system, pluripotent embryonic progenitor cells, pluripotent adult progenitor cells, multipotent embryonic progenitor cells, multipotent adult progenitor cells, cells of the hematopoietic system, cells of the immune system and/or cells of the muscle system. The cells are preferably selected from:

established cell lines and primary non-pathological animal cultures, including human, such as for example: neurons, glial cells, non-glial cells, osteoblasts, osteocytes, osteoclasts, chondroblasts, chondrocytes, fibroblasts, keratinocytes, melanocytes, glandular cells, corneal cells, retinal cells, mesenchymal stem cells, hematopoietic stem cells, embryonic stem cells, epithelial cells, platelets, thymocytes, lymphocytes, monocytes, macrophages, myocytes, hepatocytes, renal cells, urethral cells, cardiomyocytes, myoblasts and/or germ cells.

established cell lines and the primary pathological human cultures such as: acute myeloid leukemia (THP-I), breast cancer (T47D, MCF-7, MDA-MB-438), prostate cancer (DUI45, Lncap, PC3), colon cancer (Hs 675.T), glioma (U87), bone cancer (Saos-2), primary tumor melanoma (A375), metastatic melanoma (HS294), adenocarcinoma (HeLa, TAC-I), kidney carcinoma (Hs I95.T), carcinoma (C-4I), chondrosarcoma (Hs 8I9.T), fibrosarcoma (HT-1080), glioblastoma (A172, OR-138 MG, LN-18), leukemia (SUP-B15), lymphoma (1A2), neuroblastoma (CHP-212, IMR-32, SHSY5Y, SK-N-MC), osteosarcoma (MG-63), rhabdomyosarcoma (TE 441.T), etc.

primary/established pathological non-human cell lines: metastatic melanoma (B16F10), primary tumor melanoma (C32TG), myeloma, connective tissue cancer (MM37T), breast cancer (MM2MT), prostate cancer (R3327-G), carcinoma (CT26.WT), fibrosarcoma (MM47T), glioma (F98), leukemia (BB88), lymphoma (WEHI-231), neuroblastoma (NB41A3), osteosarcoma (UMR-106), etc.

Cell restoration relates to the recovery of the cell activity of those cell cultures the metabolism of which was reduced.

An object of the present invention relates to a cell transport system characterized in that it comprises a cell support, cells and an agarose and agarase mixture, which assures cell integrity and viability during the transport process. In said system, the transported cells belong to any cell type, being selected from the group of adherent cells, semi-adherent cells and non-adherent cells.

Said cells are preferably animal cells selected from the group of human, murine, canine, bovine and/or ovine cells. In terms of the cell type, the cells of the transport system of the present invention are selected from the group of cells of the central nervous system, cells of the peripheral nervous system, cells of the dermo-epithelial system, cells of the osteoarticular system, pluripotent embryonic progenitor cells, pluripotent adult progenitor cells, multipotent embryonic progenitor cells, multipotent adult progenitor cells, cells of the hematopoietic system, cells of the immune system and/or cells of the muscle system. The cells are preferably selected from the group of neurons, glial cells, non-glial cells, osteoblasts, osteocytes, osteoclasts, chondroblasts, chondrocytes, fibroblasts, keratinocytes, melanocytes, glandular cells, corneal cells, retinal cells, mesenchymal stem cells, hematopoietic stem cells, embryonic stem cells, epithelial cells, platelets, thymocytes, lymphocytes, monocytes, macrophages, myocytes, hepatocytes, renal cells, urethral cells and/or germ cells. Established cell lines derived from primary cell types, stable cancer cell lines and standard cell lines of the Caco2, MDCK, Jurkats type, etc., are also included.

In a particular embodiment, the cells are neurons.

In another particular embodiment, the cells constituting this first object of the invention are genetically modified.

In another particular embodiment, the cells constituting this first object of the invention are genetically modified neurons.

In the system constituting this first object of the invention, the cells can be transported both cultured in the form of a monolayer to which the agarose and agarase mixture is added and in suspension, embedded in the agarose and agarase mixture.

The cell support can have any cell culture format, preferably selected from the group comprising plates, flasks, culture chambers, tubes, bottles and/or transwell-type asymmetric supports. In a particular embodiment, the surface of the support includes components of the extracellular matrix that increase the capacity of adherence of the cells to the support.

The agarase concentration is between 60 and 90 units per milliliter of 1% agarose, preferably 80 units per milligram of 1% agarose.

The agarose used is low melting point agarose, its melting point preferably being close to 42° C. In said transport system, the final agarose concentration used is 0.2 to 0.6%, preferably 0.5%.

In a particular embodiment, the transport system constituting this first object of the invention comprises a mixture of low melting point agarose at a concentration of 0.2 to 0.6% and agarase at a concentration of 80 units per milliliter of 1% agarose. In a preferred embodiment, this agarose and agarase mixture remains in semi-solid state at temperatures of not more than 25° C. In another preferred embodiment, said mixture remains in liquid state when the agarose is digested by the agarase. The agarose and agarase mixture is removed from the cell support leaving the cell culture ready to be used in different applications.

The cell transport system constituting this first object of the invention allows the extraction of the cells of the transport system by means of basic cell culture techniques.

Likewise, the transport system of this first object of the invention assures cell viability and integrity of at least 85% of the cultured cells.

A second object of the invention relates to a method for the transport of cells involving the use of the aforementioned transport system, said method comprising preparing the transport system, constituting the first object of the invention, transporting and recovering the cells.

In said method, the step of preparing the cell transport system comprises the steps of:
  a. Seeding the cell culture.
  b. Preparing the agarose-agarase mixture.
  c. Adding the mixture of step b to the cell culture.
  d. Solidifying the agarose-agarase mixture.
  e. Sealing the transport system.

In this second object of the invention, preparing the agarose and agarase mixture used in the previous step b, in turn comprises the steps of:
  i. Mixing the agarose solution in the culture medium specific for the type of cell culture to be transported at the established concentration, as described in the first object of the invention.
  ii. Adding the agarase at the established concentration in the first object of the invention to the agarose solution of step i
  iii. Homogenizing the mixture In one embodiment, the step of adding the mixture of step b to the cell culture involves coating the monolayer cultured cells with the agarose-agarase mixture, and in another embodiment it involves the homogenous mixture of the cells in suspension with the agarose-agarase mixture.

The step of solidifying the agarose and agarase mixture is carried out in a particular embodiment at a temperature of less than 37° C. in a period of 15-30 minutes.

In this method constituting the second object of the invention, the transport is carried out in a particular embodiment at temperatures of not more than 25° C., the transport time preferably being not more than 60 hours at a temperature range between 18 and 23° C., more preferably at 22° C., during a time of not more than 72 hours. The viability of the cells is of at least 85%.

In this method constituting the second object of the invention recovering the cells in turn comprises the steps of:
  f. Digesting the agarose, agarase mixture.
  g. Removing the transport medium and replacing it with culture medium.
  h. Restoring the cell culture.

Specifically, digesting the agarose-agarase mixture comprises: incubating the transport system at 37° C. for a time period between 1.5-2 hours, adding tempered culture medium and incubating the system for an additional hour at 37° C. In a particular embodiment when the cells are in suspension, digesting the agarose and agarase mixture comprises an additional step involving centrifuging the system at 800-1000 g.

In an embodiment, step h) involves incubating the cells at 37° C. and 5% of $CO_2$.

In a particular embodiment of this second object of the invention, prior to their use, the cells are extracted from the support transporting them; in another particular embodiment, the cells remain in the support transporting them.

Another object of the invention relates to the use of the transport system constituting the first object of the invention for the transport of cells.

Another object of the invention relates to the use of the transport system constituting the first object of the invention for carrying out cell and/or molecular biology assays. In a particular embodiment, said assays are selected from the group comprising the testing of drugs, biomaterials and nanoparticles, functional assays, morphological studies, studies for characterizing gene expression, studies for characterizing protein expression.

Another object of the invention in the present application is the incorporation of the transport system in a transport box and the transport system—transport box assembly derived from said incorporation.

The transport box or support will consist of any structure able to maintain for at least 75 hours the cell system transported at a constant temperature of 22° C., and which furthermore provides the system with the necessary protection against mechanical movements and oscillations occurring during the transport period.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the agarose concentration range determined for transport based on the final consistency of the mixture and on the degree of difficulty of cell recovery from the prepared mixture. The solid line represents the strength of the transport mixture; the greater the agarose concentration of the transport mixture, the greater strength the mixture will also provide to the system and therefore the transport is done in more reliable conditions. The dotted line represents the degree of difficulty for carrying out cell recovery; the greater the agarose percentage/concentration, the more difficult cell recovery is due to the high rigidity of the system. Therefore, it is necessary to establish a final agarose concentration range which assures transport in a reliable manner and at the same time facilitates the recovery of the culture after transport. Based on the assays performed with the different agarose concentrations (%), it has been established that the optimal agarose concentration range for transport is 0.2-0.6%, indicated in the figure with the shaded box.

The images obviously show that none of the concentrations of the agarose and agarase mixture used in the assay affects cell integrity and morphology when compared with the culture that has not been in contact with the mixture (control). The combination of agarose and agarase in the transport medium assures optimal recovery of the cells.

Figure 3:
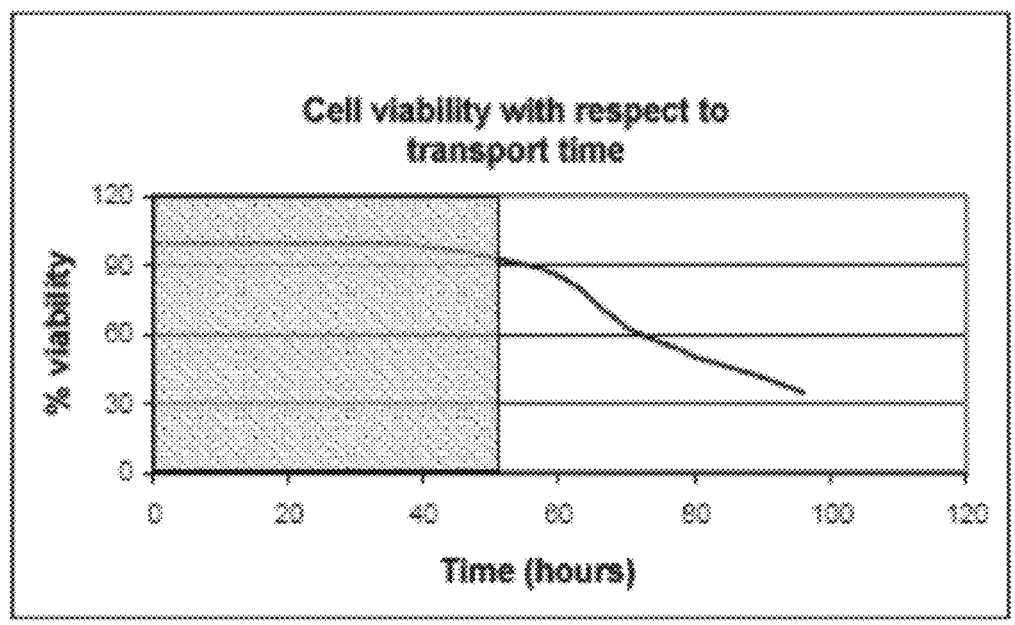

FIG. 3: Determination of the transport time

FIG. 3 shows the cell viability of the culture of the SK-N-MC cells when it is exposed to the agarose and agarase mixture over time. During the first 48 hours in contact with the mixture and in the conditions determined for transport, the viability of the culture is not affected; however, after 48 hours the cell viability starts to decrease and after 72 hours in the conditions described the cell viability shown is 60%. After 96 hours in culture, the cell viability is quite affected, with a survival rate close to 30%.

Figure 4:
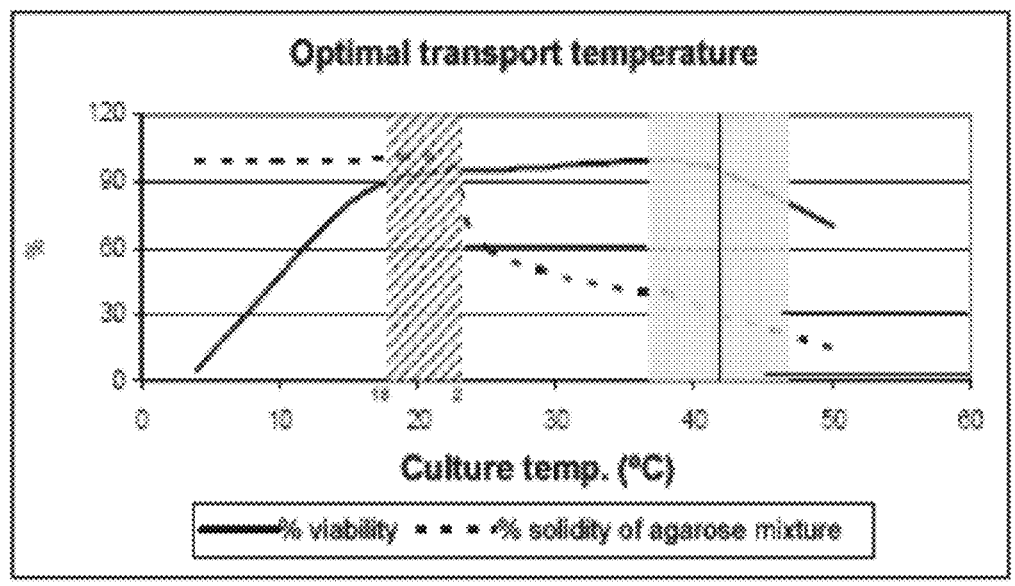

FIG. 4: Determination of the optimal transport temperature.

FIG. 4 graphically shows the determination of the optimal transport temperature based on the criteria described: cell viability, consistency of the transport medium and activity of the agarase enzyme. The solid line represents cell viability with respect to the temperature of culture; the optimal temperature for maintaining human cells in culture is 36-38° C.; however, the cell viability is not dramatically affected within the range of 20-40° C. The dotted line represents the integrity or solidity of the mixture of agarose with agarase and medium; from 25° C. the gelled transport medium loses consistency and does not assure a reliable cell transport; therefore based on the consistency of the transport medium the temperature should not reach 25° C. The vertical line represents the optimal action temperature of the agarase enzyme, and the shaded area seen on both sides of this line corresponds to the temperature range in which the enzyme is still active. Therefore, the optimal transport temperature will be the temperature at which cell viability is as close as possible to 100%, taking into account that the agarose-agarase mixture maintains a firm consistency and furthermore, the agarase enzyme is not active. This temperature is 18-23° C., as shown by the striped area defined in the figure.

FIG. 5: Graphic representation of the design of the cell transport system.

FIG. 5a relates to the plate/flask transport model for adherent cells. In this case the cells are cultured in plate or flasks suitable for the final application of the culture and once the cells have correctly adhered and show a normal morphology, the culture medium is removed and the agarose plus agarase mixture which will act as a protective medium of the cells during the transport period is applied on them.

FIG. 5b shows the scheme of the plate/flask model for cells in suspension and adherent cells the transport of which is carried out with those included in the agarose and agarase mixture.

Finally, FIG. 5c shows the tube transport model, in which it is possible to transport any cell type, adherent or not, because the cells, as shown in FIG. 5b, are embedded in the agarose plus agarase mixture.

The election of each of the models will depend on the characteristics of the cell type object of transport and on the final application of the product, i.e., on the type of analysis that has to be performed with the cells.

FIG. 6: Toxicity study of the cells subjected to the agarose and agarase mixture The graphs show the cytotoxicity curves of AMSC (adipose tissue-derived mesenchymal stem cells) cells, CHO cells, MDCK-II cells, MDCK-II-MDR1 cells, fibroblasts, keratinocytes and SK-N-MC neuroblastoma cells after contact with the agarose plus agarase mixture.

The groups included in the assay are the following: culture: cells maintained in standard culture conditions; 37° C., 5% $CO_2$ and normal culture medium; control: cells subjected to the transport conditions, i.e., 20-22° C., outside the incubator but with normal culture medium; and agarose plus agarase mixture: cells subjected to the transport conditions, i.e., 20-22° C., outside the incubator but in the system of the invention.

As can be seen in the graphs, the cells subjected to the transport system did not show differences in terms of the proliferative capacity with respect to the control and to the culture, which indicates that the cells have not experienced cytotoxic effects during the time they were maintained in the transport system of the invention.

FIG. 7: Study of the cell morphology after exposure to the agarose plus agarase covering or envelope These figures show the photographs of the AMSC (adipose tissue-derived mesenchymal stem cells) cells, CHO cells, MDCK-II cells, MDCK-II-MDR1 cells, fibroblasts, keratinocytes and SK-N-MC neuroblastoma cells after exposure to the agarose plus agarase mixture.

Figure 7A:
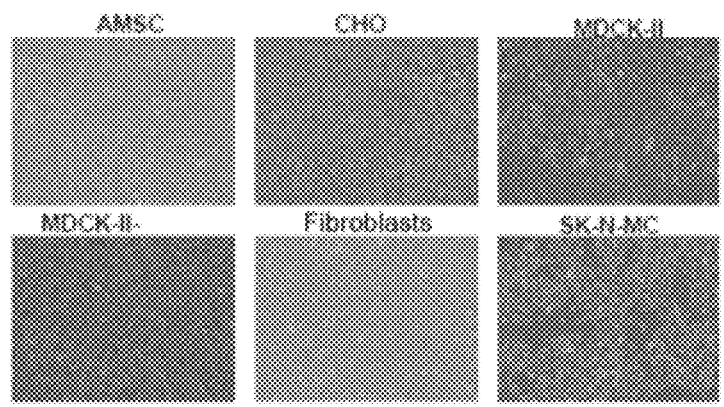

FIG. 7a shows the morphology of the cells before the agarose plus agarase mixture is applied to them.

Figure 7B:
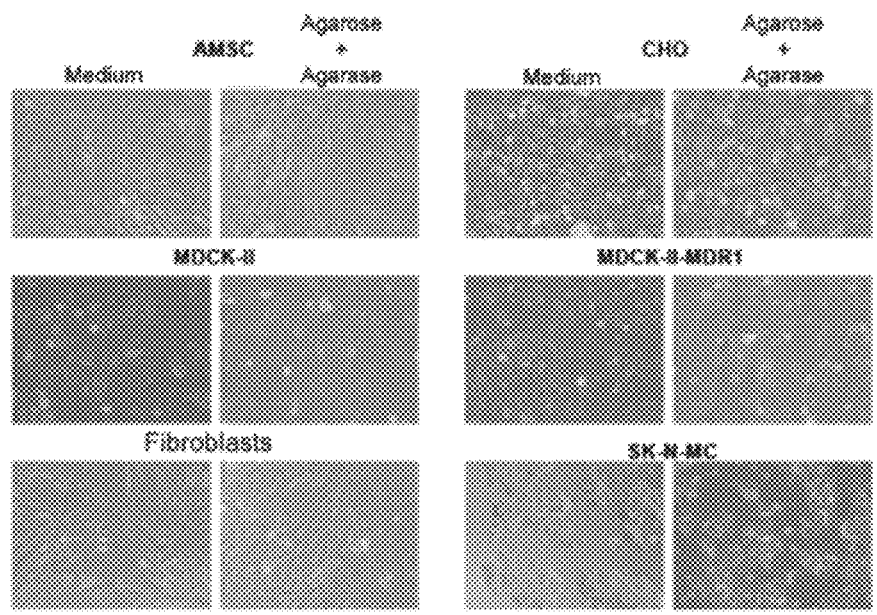

FIG. 7b shows images of the cells which have the agarose plus agarase covering on the monolayer culture, and they are compared with those which only contain the culture medium.

Finally, in FIG. 7c, it is possible to compare the morphology of the cells which are growing in normal culture conditions (culture), the control cells (which have been subjected to the transport conditions at 20-22° C., outside the incubator but cultured in normal culture medium) and the cells which have been treated with the agarose plus agarase covering in the transport conditions (20-22° C., outside the incubator), 24 hours later.

As shown in the figures, the cell morphology of the different cell types is not affected by the covering or envelope of the agarose plus agarase mixture. The morphology of the cells exposed to the mixture of the transport system does not vary during exposure to the mixture, not even after it is removed.

FIG. 8: Increase of cell adhesion with laminin

Figure 8A:
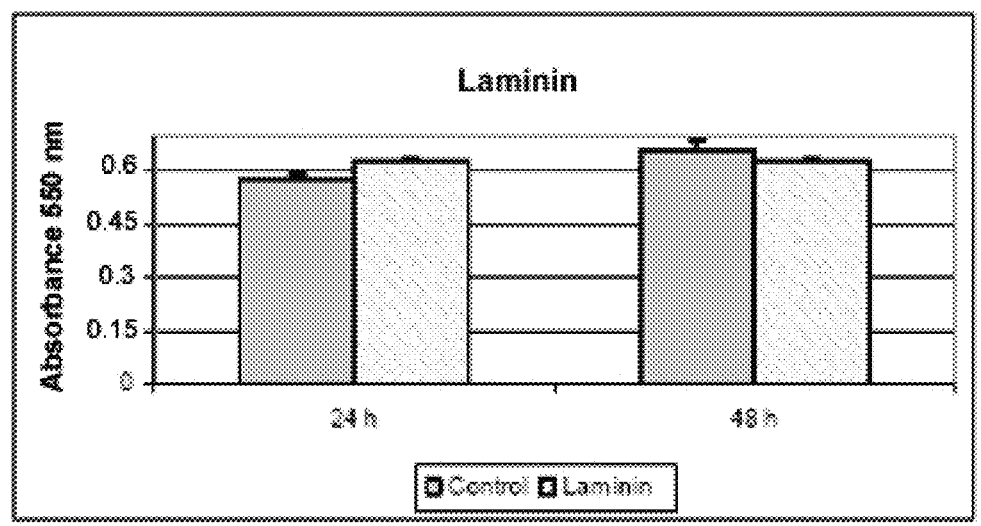
Figure 8B:
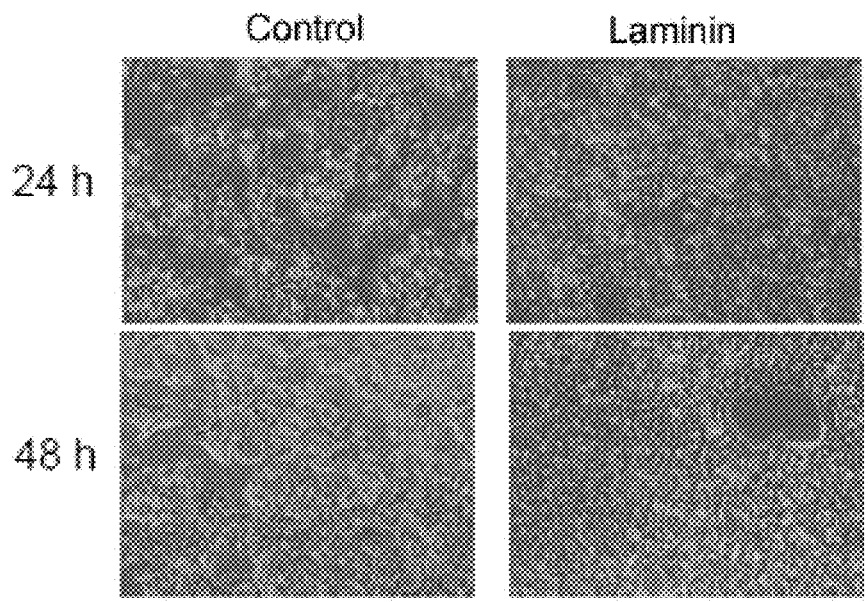

FIG. 8 shows the effect of the use of supports treated with laminin on the proliferation and morphology of the SK-N-MC cells. FIG. 8a corresponds to the analysis of the proliferative capacity of the SK-N-MC cells cultured in standard 24-well plates (control) and 24-well plates treated with laminin (laminin). After 24 hours in culture the proliferation rate of the cells grown in the plates with laminin is greater than that shown by the control cells. After 48 hours in culture, the proliferation rates match up, probably due to the high confluence of the culture in which the proliferation has reached its maximum level. This increase in the cell proliferation in the culture with laminin is due to a larger number of cells adhered to the support thus increasing the number of cells that proliferate. FIG. 8b clearly shows the positive effect of laminin on cell adherence; a larger number of cells is observed in the plates treated with laminin despite the fact that the number of cells initially seeded was identical for the control plates and the plates treated with the laminin.

Figure 9:
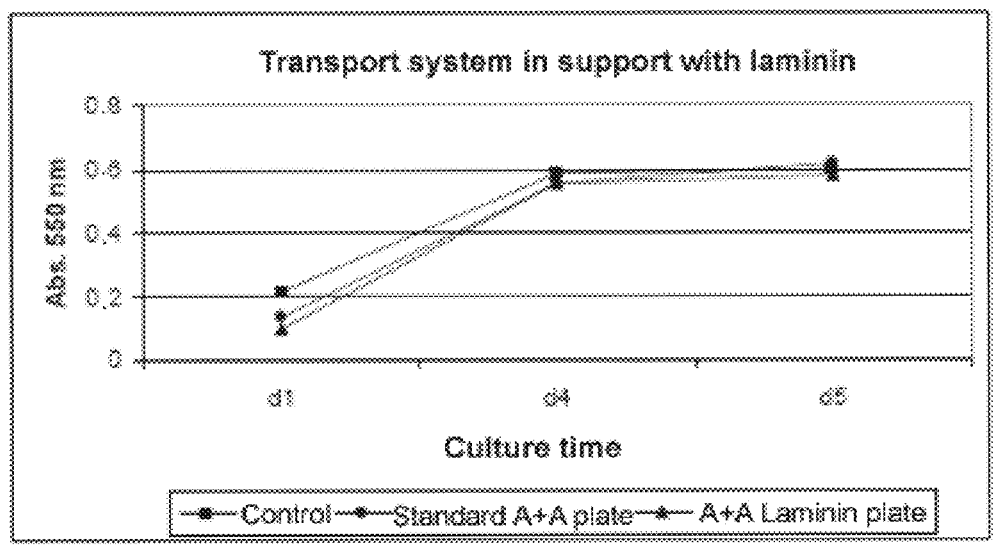

FIG. 9: Study of the proliferative capacity of the transport system in the support with laminin The present figure shows the proliferative capacity of the SK-N-MC cells after they are cultured in standard culture plates and plates treated with laminin. No differences in the proliferation are observed in any of the assayed groups, i.e., no differences in the cultured cells in the transport system with or without laminin nor with respect to the control are observed.

The assayed group are the following: control group: cells cultured in standard culture conditions 37° C., 5% $CO_2$ in normal medium; standard A+A plate group: cells subjected to the transport conditions (20-22° C., outside the incubator) with the agarose plus agarase mixture, but without laminin; and A+A laminin plate group: cells subjected to the transport conditions (20-22° C., outside the incubator) with the agarose plus agarase mixture with laminin.

FIG. 10: Increase of cell adhesion with poly-L-lysine in the transport system

The graphs of FIG. 10 show the cytotoxicity curves of the SK-N-MC cells after contact with the surface treated with poly-L-lysine at different concentrations.

Figure 10A:
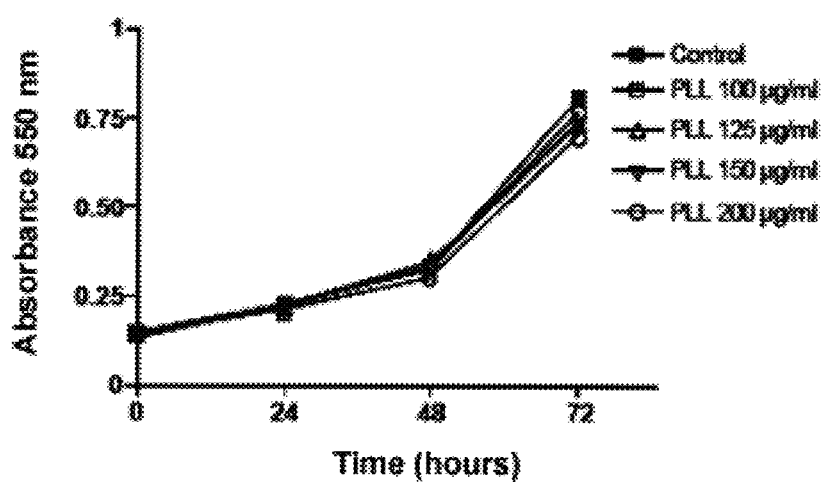
Figure 10B:
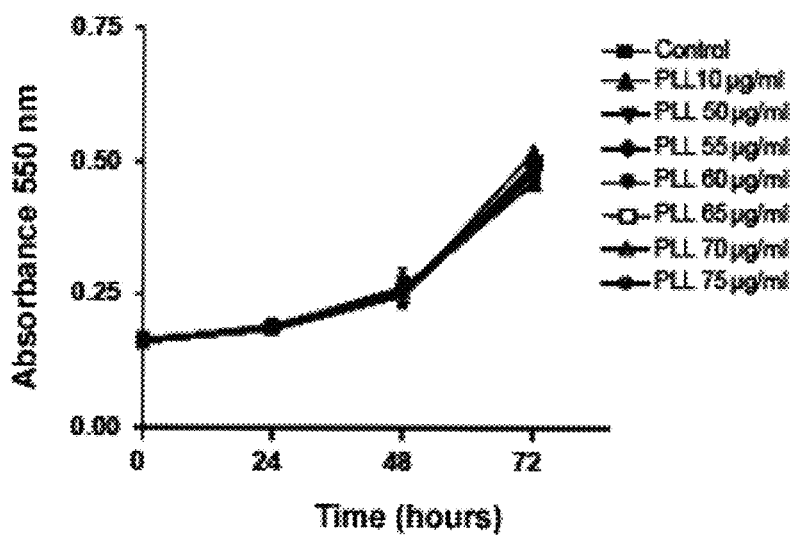

FIG. 10a shows the upper poly-L-lysine concentration range (100-200 μg/ml) assayed. In contrast, FIG. 10b shows the lower poly-L-lysine concentrations (10-75 μg/ml) assayed.

As can be observed in the graph in FIG. 10A, the increasing poly-L-lysine concentrations show a reduction in the proliferative capacity of the SK-N-MC cells. FIG. 10b shows that the cultures exposed to the lower poly-L-lysine concentrations show a proliferation kinetics that is virtually unchanged with respect to that observed in the cells not exposed to poly-L-lysine.

From these results it is concluded that despite the fact that none of the concentrations dramatically affects the integrity or proliferative capacity of the culture, from the poly-L-lysine concentration of 75 μg/ml, cell proliferation seems to be reduced at 72 hours. Therefore, the poly-L-lysine concentration range in the transport system is 10-75 μg/ml, preferably 50-70 μg/ml, considering the final preferred concentration of 60 μg/ml.

FIG. 11: Morphological verification of the cell culture after contact of the surfaces treated with different poly-L-lysine concentrations FIG. 11 shows the appearance of each of the cultures used during the exposure to poly-L-lysine. The control corresponds to the cells that have been cultured in plates lacking treatment, and maintained in the same conditions as the cells in contact with poly-L-lysine, but which have not had any contact with the assayed molecule. The analysis was carried out during 96 hours.

Figure 11A:
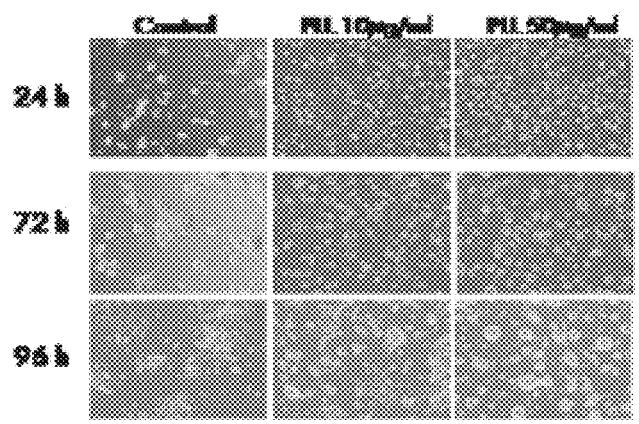
Figure 11B:
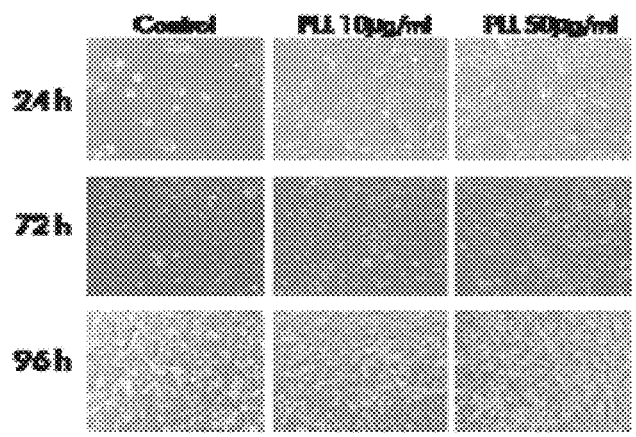
Figure 11C:
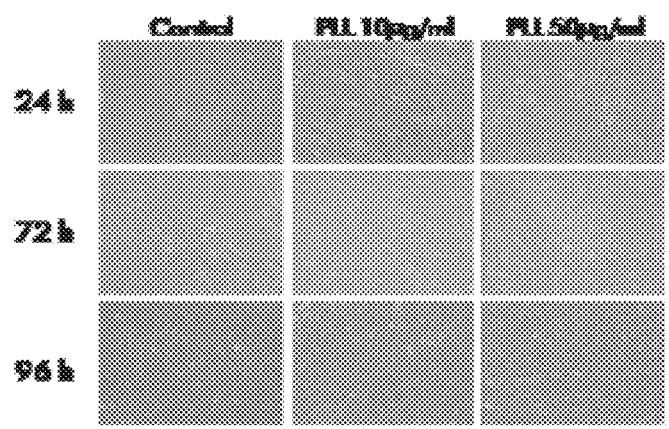
Figure 11D:
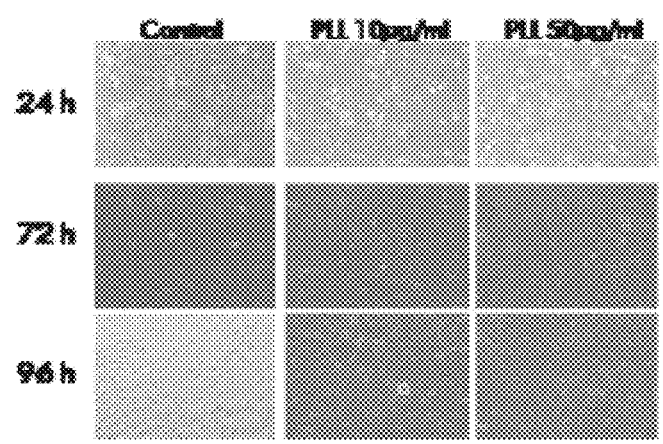

FIG. 11a shows the images corresponding to the SK-N-MC cell cultures, FIG. 11b shows the MDCK-II-MDR1 cells, the cells shown in FIG. 11c are human mesenchymal cells, and finally, the morphology of the human articular chondrocytes is shown in FIG. 11d.

In the images corresponding to this assay, it can be seen that there is no difference at all between the cell morphology of the cultures exposed to poly-L-lysine and the morphology of the cells not exposed to contact with said molecule.

Figure 12:
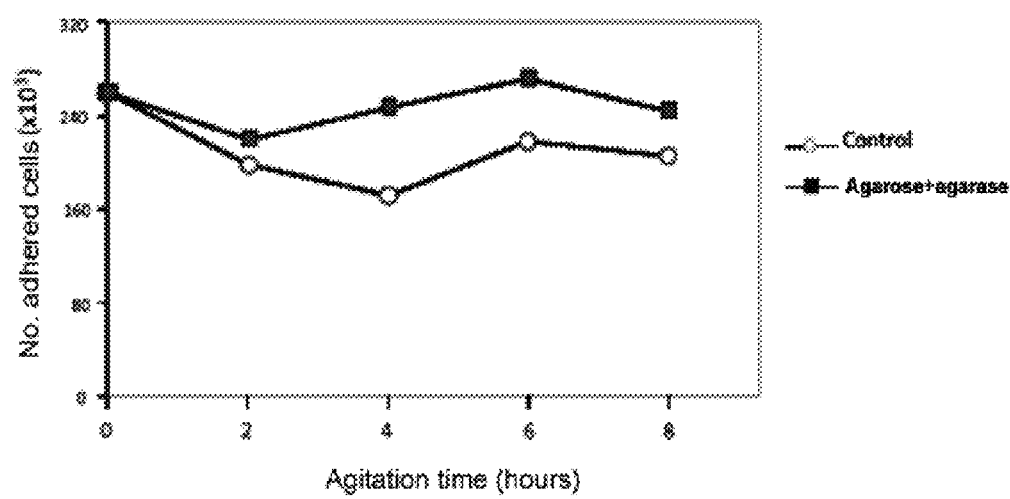

FIG. 12: Protection of the transport system from mechanical agitation

FIG. 12 shows the number of cells collected from the wells that contained medium (control) and which contained the transport mixture (agarose+agarase) during the agitation period (hours). All counts were done in triplicate.

FIG. 12 shows the number of cells that remained adhered to the culture surface during the time in agitation. In this figure, it can be seen how the number of cells recovered from the wells in which the covering was applied during agitation (agarose+agarase) was greater than that collected from the wells in which the agitation was completed containing only culture medium (without the agarose plus agarase covering).

FIG. 13: Application of the cell transport system to three-dimensional culture systems: analysis of the integrity of the cell monolayer after removing the covering.

Figure 13A:
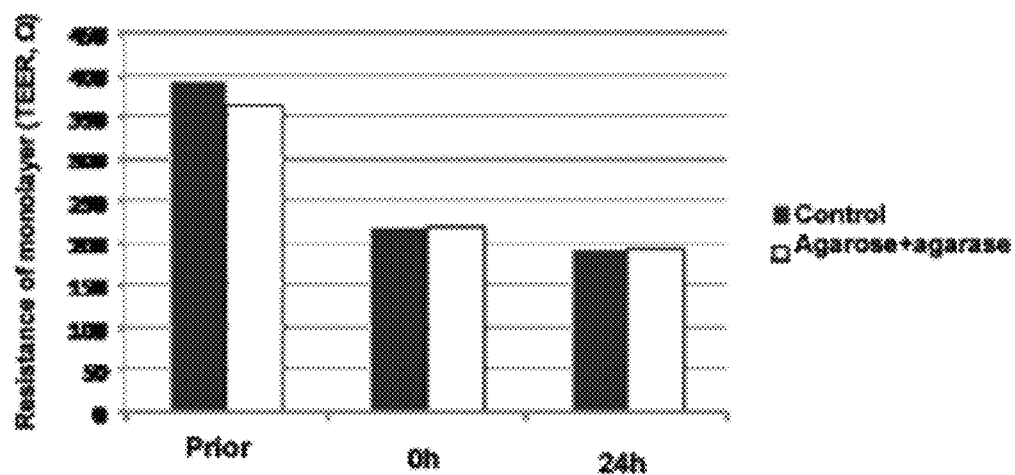

FIG. 13a shows the resistance values (TEER) obtained from the measurement of the control wells which were exposed to the mixture. It shows three different measurements which correspond to the moment prior to adding the agarose plus agarase covering on the culture (prior), the moment immediately after the covering is removed (0 h) and 24 hours after the agarose plus agarase is removed (24 h). The reading was performed in 12 wells for each of the two different conditions; control wells with medium and wells with agarose plus agarase covering.

Figure 13B:
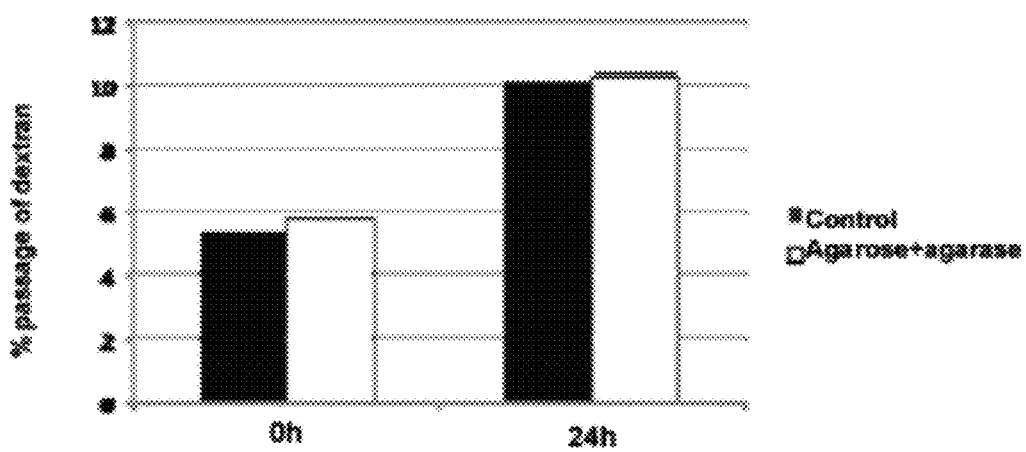

FIG. 13b shows the percentage of the dextran detected in the wells in the basal position, i.e., the percentage of dextran that traversed the cell monolayer. Two readings were performed, the first one corresponding to the moment immediately after the covering is removed (0 h) and the second one 24 hours after the agarose plus agarase mixture is removed (24 h). The analysis was carried out in 12 wells for each of the two different conditions; control wells with medium and wells with agarose plus agarase covering.

DETAILED DESCRIPTION OF THE INVENTION

The transport system described in the present invention, proposes a cell transport system that allows transporting cells in culture, adhered or in suspension, with maximum quality standards and viability and which does not necessarily require the receiving laboratory to have an infrastructure and skilled personal for the recovery of the cell culture if the final application of the transported cells does not require this.

The transport medium of the invention consists of a specific agarose and agarase mixture that can be applied to any type of cell culture, either cultured in monolayer, in 3D or in suspension. The system can therefore be applied to any cell type of a different origin such as: human, murine (rats, hamsters, mice), canine, bovine, ovine, etc. The cells transported by this system can be genetically modified cells.

The transport system of the present invention can be incorporated in any portable conditioning device able to maintain the temperature range during the transport time regardless of the room temperature.

Said portable conditioning devices are known in the state of the art as transport box and consist of any structure able to maintain for at least 75 hours the transported cell system at a constant temperature of 22° C., additionally providing the system with the protection necessary against mechanical movements and oscillations occurring during the transport period. Examples of transport boxes existing in the state of the art for the purpose of the present invention include: "Insulated box P650" and "KF TermoCell 22" marketed by Kern Frio S. A.

Both references consist of insulated transport systems which allow constantly maintaining the desired temperature (20-22° C.), with minimal variations (±2° C.)

Once said transported cells reach their destination and the agarose and agarase mixture in gel is removed, the cells can be extracted from the support transporting them or be used in the support transporting them. Likewise, the transport system of the present invention can be applied to any type of cell culture format or support, such as for example: culture plates (with 6, 12, 24, 96, 384 wells, etc.), culture flasks (25, 75, 175 cm², etc.), culture chambers or tubes (of 1.5, 15, 50 ml, etc.), bottles, etc., so the following are contemplated as possible applications of the transport system:

functional assays: cytotoxicity assays for the analysis of new molecules, drugs, biomaterials and nanoparticles; proliferation assays; apoptosis assays; studies of the secretion of molecules, proteins, growth factors, proteoglycans, mucopolysaccharides . . . ; cell differentiation and response assays, membrane marker expression studies; etc.

morphological studies: histological assays, immunohistochemical assays, SEM and TEM analysis.

studies for characterizing gene and protein expression: extraction of nucleic acids directly on the cells supplied in the system, extraction of proteins directly on the cells supplied in the system, etc.

In other words, based on the subsequent use of the cell culture that is to be carried out in the receiving laboratory, the transport system is adaptable to any transport format or support (plates, tubes, flasks, culture chambers, bottles, tranwell-type asymmetric supports etc.) and to the cell density of the culture, because each cell type requires being cultured at specific densities depending on the format of the transport system and on the type of assay to subsequently be performed.

In one embodiment, the transport system comprises cells of the nervous system. Said cells can be genetically modified cells. The genetic modifications can be related to neurodegenerative diseases (Alzheimer's, Parkinson's, Creutzfeldt-Jakob, multiple sclerosis, etc.), epilepsies, diseases of the peripheral nervous system (Guillain-Barré Syndrome, Charcot-Marie-Tooth Disease, etc.), etc.

In a particular embodiment, the transport system comprises genetically modified neurons. The mutation of said neurons is associated with Alzheimer's disease.

In order for the cell transport system of the present invention to provide the mentioned advantages, the medium in which this transport is carried out must be easy to handle in the moment of seeding the cells. Likewise, the transport medium must provide the system during the transport with sufficient strength to maintain cell viability in optimal conditions during the entire time transport lasts, i.e., preventing alterations of both the morphological and functional properties in the transported cells from occurring.

As a result, it is ideal for the system to be integrated by a transport medium the physical characteristics of which can vary in a simple and controllable manner, such as for example in response to temperature changes. In other words, at temperatures at which the transport is carried out, 18-23° C., the material behaves like a solid or semisolid to maintain the strength of the system, preventing the sustained movements occurring during the transport from finally affecting the integrity, and said solid or semisolid state from being able to be reversed by means of a temperature change, at 37° C., facilitating cell culture handling and recovery in conditions of cell viability of more than 85%.

As previously mentioned, agarose, which consists of alternating (1-3) linked β-D-galactose and (1-4) linked (3-6)-anhydrous-α-L-galactose copolymers, is a thermally reversible polysaccharide, i.e., it can be melted or gelled based on the temperature to which it is subjected and is commonly used for cell encapsulation.

The state of the art describes how agarose is commonly used for three-dimensional cell culture (references 1 and 2) as a support of culture. For carrying out the recovery of the cells included in the agarose used as a culture support, the three-dimensional structure is treated with an agarase solution which, once added to the support, digests the agarose in which the cells are growing, thus allowing cell recovery.

In contrast, the system of the present invention allows cell transport in a system that is ready to be used and, where appropriate, the possible subsequent recovery of the transported cells using a simple methodology.

In the state of the art, the use of agaroses commonly applied in the three-dimensional culture system involves the transported cells necessarily being subjected to temperatures of more than 65° C. for facilitating the removal of the agarose and thus allowing the release of the cells forming the transported culture.

However, the temperature of 65° C. to which the culture must be subjected would be too aggressive and cause the death of the cell culture because the optimal growth temperature of animal cells is 36-38° C. Above this optimal temperature (hyperthermia conditions) cell viability is affected, irreversibly damaging the integrity of the cells of the culture. In contrast, temperatures below the optimal temperature, hypothermia, are better tolerated by the cells than high temperatures are. In the case of the application of a temperature of less than the optimal recommended temperature, decreased cell metabolism occurs, the cell reactions (proliferation, metabolisms, growth, . . . ) slow down but the cell maintains its integrity, and when optimal thermal conditions for growth are restored, the cells recover their normal cell activity. Therefore, hypothermia is a widely used methodology for slowing down the growth of microorganisms and tumor cells.

In the system described in the present invention the transport medium comprises an agarase and agarose mixture which facilitates cell recovery, meaning that this process is carried out in a simpler manner, incubating the transport system formed by the support containing the cells to be transported at the temperature at which the agarase enzyme is active. The agarose is thus digested, allowing cell recovery.

One of the advantages of the system of the invention consists of the fact that the digestion is carried out homogeneously because the agarase is also incorporated homogeneously to the agarose solution. Digestion thus begins homogeneously in the agarose solution when it is incubated at the suitable temperature for the agarase enzyme to act. This involves less recovery time and greater viability of the recovered cell culture.

In addition, the fact that the agarase is incorporated in the transport system facilitates the standardization of preparing the transport system according to the cell type and format or cell support and of the cell recovery.

Likewise, the incorporation of agarase in the transport system prevents the receiving laboratory from needing to use the enzyme independently, simplifying the cell recovery process and enabling the use of the system in very different laboratories that do not have specific knowledge in the corresponding techniques.

The agarose which is used in the present invention is a low melting point agarose having a low melting temperature, close to 42° C., which has a significant advantage with respect to using the agaroses commonly used in cell cultures (with melting points of approximately 65° C.) because it puts the melting point of the agarose at a temperature close to the optimal temperature for growth of the cell culture.

Low melting point agaroses are available on the market, including Ultra Pure® low melting point Agarose marketed by Invitrogen, NuSieve® GTG® Agarose marketed by Lonza, LM Agarose and LM Sieve marketed by Pronadisa, Agarose SERVA Premium low melting, Agarose SERVA for PCR low melting and Agarose SERVA low melting marketed by Serva.

According to the aforementioned state of the art, the melting of the low melting point agarose at 42° C. as described in its specifications brings forth the problem of not achieving complete, but rather partial, melting of the agarose applied to the cells, which makes it difficult to separate the agarose from said cells, negatively affecting correct cell recovery. In these cases, the application of a higher temperature to complete the melting of the agarose would significantly affect cell survival because the temperature used (>45° C.) exceeds the range in which the cells still maintain their integrity.

Therefore in order to facilitate the recovery of the transported cells and maximally optimize the system, it is necessary to promote complete separation of the agarose from the cells of the culture. This is achieved by means of the system proposed by the present invention.

Agarase is an enzyme with a molecular weight of 32 kDa that hydrolyzes the [1-3] linkages between D-galactose and 3,6-anhydrous-L-galactose residues of agarose. In order for agarase to be able to carry out the previously described hydrolysis, it needs to be activated. The temperature at which the agarase enzyme shows its maximal activity is 43° C., but as occurs for most enzymes, there is a range above and below this optimal temperature in which the activity shown by the enzyme is also important. In the case of the agarase enzyme, it is observed that this activity is detectable at the temperature of 37° C., but not at 30° C. Finally, the temperature range in which agarase has substantial activity is 37-42° C.

The transport medium of the present invention comprises an agarose concentration in the final mixture of 0.2-0.6%, preferably 0.5%, and an agarase concentration of not more than 90 units per milliliter of 1% agarose, preferably 80 units per ml of 1% agarose.

Therefore, the following aspects are contemplated in the development of the transport system proposed by the present invention: (i) culturing the selected cells for their conditioning and adhesion in the selected format, (ii) applying the agarose-agarase mixture to create the transport system, (iii) transport conditions, (iv) cell recovery after the transport process, (v) verifying the maintenance of cell integrity after transport in the system described in the invention by means of measuring cytotoxicity and cell morphology.

i. Culturing the Selected Cells for their Conditioning and Adhesion

As previously mentioned, the system allows the transport of any cell type, including genetically modified or non-genetically modified cells. Said cells can be transported cultured in monolayer, 3D, adhered or embedded inside the agarose and agarase mixture (FIG. 5). The cells will be prepared specifically for each of these options.

1. Cells in Monolayer:

The cells of the selected cell type are seeded in the plate or flask having the suitable format for carrying out the final application. They are cultured in the specific temperature conditions, moisture conditions, atmospheric conditions and culture medium for their optimal growth and are maintained in culture long enough for the cells to adhere to the plastic and acquire optimal cell morphology, usually incubation overnight should be enough.

There are semi-adherent cell types which have a general characteristic of showing little capacity of adherence to common cell culture supports, such as for example SK-N-MC cells, etc. To prevent this type of cells from being lost in the cell recovery process after transport due to a low adherence of these cells to the support, the invention also contemplates the adaptation of the system to cell types with low adherence. To that end, the possibility of using plates or flasks treated with different molecules or components of the extracellular matrix which increase the capacity of adherence of the cells to the support, such as laminin, poly-L-lysine, collagen, etc., components of the extracellular matrix widely used to increase cell adhesion to the culture support, is considered. It has been observed that the use of poly-L-lysine for the purpose of increasing cell adherence to the culture support in the present transport system is particularly advantageous as it induces greater fixing to the culture surface without altering the morphological and physiological characteristics of the cells exposed to them.

To establish the suitable poly-L-lysine concentration in the transport system of the present invention, cell integrity after exposure of the system to increasing poly-L-lysine concentrations, as described in assay 2.4.1, was analyzed.

The results of this assay are shown in FIG. 10 and allow defining as the suitable poly-L-lysine concentration in the transport system between 10-75 µg/ml, preferably, 50-70 µg/ml, more preferably 60 µg/ml. The following step of the process is not performed until the next day, when the cells are already adhered to the surface of the plate or flask.

2. Cells Embedded in the Agarose Plus Agarase Material

The cells are maintained in standard culture conditions until reaching step ii.

ii. Applying the Agarose Plus Agarase Mixture to Create the Transport System

Depending on the format used for cell transport, the amount of mixture to be added is different. For example, in the case of the wells of a 24-well plate, the amount of mixture used in each of the wells is 1 ml, whereas for the 96-well plates it is 150 µl per well, for cells in suspension the volume of the mixture to be added will be proportional to the flask and proportional to the number of cells arranged in the support because a proportion of $1-2\times10^6$ cells per ml of mixture is maintained. Therefore, in 50 ml tubes, the amount of mixture to be used will be 20 ml, and in 15 ml tubes, 6 ml.

1. Cells in Monolayer:

The day after seeding the cells and once the desired monolayer is created, the medium is removed from the culture and the covering of the agarose-agarase mixture is applied on the cells, as described in Example 2.

The transport medium tempered at 37° C. is added by covering the monolayer of the cell culture in the plates/flasks of cells arranged in ice to prevent the agarase enzyme from acting on the agarose too soon because the optimal action temperature of the agarase enzyme is 37-42° C. The estimated time for the mixture to acquire the desired consistency is 15-30 minutes, after which the support will be sealed with parafilm on all its ends to prevent the system from opening during transport and contact of the culture with the external medium, eliminating the risk of contamination during transport.

2. Cells Embedded in the Agarose Plus Agarase Material

In this second case it is not necessary to seed the cells the day prior to transport because these cells are arranged directly in the agarose and agarase mixture, being completely mixed with the transport system.

The agarose mixture is prepared in the exact same manner as for the case of cells in monolayer, as described in Example 2. The melted agarose and next the agarase are added to a volume of medium, which will vary depending on the format selected. Once the components are homogeneously mixed in the same tube in which the transport medium is at 37° C., the amount of cells selected for transport is added and the tube is placed in ice to prevent the agarase enzyme from acting on the agarose too soon. In 15-30 minutes the agarose-agarase mixture will have acquired the suitable consistency after which the system used (tube, flask, culture chambers, etc.) will be sealed as specified in the preceding point.

Case 1 of the present invention will be exclusive for the transport of cell cultures in monolayer, whereas case 2 will be applied both to adherent cell types which are transported in suspension and non-adherent cell types (FIG. 5).

iii. Transport Conditions:

1. Transport Temperature

Another important aspect of the present invention is that of determining the temperature range in which the transport of the system can be performed because too low of a temperature could compromise cell viability, whereas too high of a temperature could endanger the integrity of the system for transport, and accordingly cell viability.

The optimal temperature range for cell transport used in the cell transport system of the invention (FIG. 4) has been determined based on the analysis of three limiting parameters such as cell integrity, integrity of the agarose-agarase mixture and medium, and the temperature at which the agarase enzyme remains inactive.

a. Cell integrity: As previously described, the optimal temperature for growth of the cell cultures is 36-38° C., although the temperature range in which the cells maintain their viability and integrity is 20-42° C.

b. Integrity of the agarose-agarase mixture and medium: in order for the cell transport used in the system of the invention to be optimal, it is necessary for the agarose-agarase mixture to provide a solid or semisolid consistency which assures protection of the cells against the continuous movements occurring during transport. It is therefore important for the transport to be carried out within a temperature range that allows maintaining the solid state of the mixture.

The consistency of the mixture is inversely proportional to the temperature to which it is exposed, the greater the temperature of exposure of the mixture, the less the integrity or solidity thereof. Upon analyzing the integrity of the mixture in a broad temperature range, it has been determined that the point of inflexion from which the mixture loses the desired consistency is around 25° C.

c. Temperature at which the agarase enzyme remains inactive: the advantage of including the agarase enzyme in the transport support mixture of the present invention consists of facilitating cell recovery once the transported cells have reached the desired destination, but it is not advisable for the enzyme to act during transport. The temperature at which the agarase enzyme shows its maximum activity is 43° C., but as occurs for most enzymes, there is a range above and below this optimal temperature in which the activity shown by the enzyme is also important. In the case of the agarase enzyme, it has been observed that this activity is detectable at a temperature of 37° C., but not at 30° C. Therefore, it is advisable for the transport support to not exceed the temperature of 30° C. after which its action is activated, and thus preventing the enzyme from acting before it is expected to.

Therefore, after testing the behavior of the system against different temperatures in a range of 18 to 28° C. and taking into account cell integrity, consistency of the mixture of the support and the activity of the agarase enzyme, the optimal transport temperature, as shown in FIG. 4, is not more than 25° C., preferably being between 18 and 23° C., more preferably at 22° C.

2. Transport Time

The maximum transport time is determined by means of the exposure of the cells covered with or embedded in the transport medium for the time transport may last. As shown in FIG. 3, the cells transported during 48 hours in the transport system of the invention have a viability of 100%, once they have been recovered after the transport process. After 60 hours, cell viability continues to be greater than 85%, i.e., within the required optimal viability range. After 72 hours of applying the system, cell viability decreases to 60%. Said value is acceptable in specific cases due to the fact that 60% cell viability allows efficiently recovering the culture. After 96 hours in culture, cell viability is now quite affected, with a survival rate close to 30%.

Therefore, a preferred embodiment of the present invention, in which said system maintains the desired quality standard, consists of the transport temperature being below 25° C., preferably 18 to 23° C., more preferably at 22° C., and the maximum transport time not exceeding 60 hours, more preferably 48 hours.

iv. Cell Recovery after the Transport Process

One of the features of the transport system of the invention is allowing the cell recovery of the transported cells. The method used for carrying out the recovery of the cell culture varies depending on the format or support used for cell transport:

When the cells have been seeded in monolayer on a surface, and then coated with the agarose-agarase mixture (according to FIG. 5a), the cell recovery process must abide by the following indications:

In the moment in which the cells are received in the laboratory of destination, they are introduced in the incubator at 37° C. and 5% $CO_2$ during a period of 1.5 to 2 hours.

After incubating at 37° C., the plate is recovered from inside the incubator and culture medium tempered at 37° C. is added to the agarose-agarase covering to facilitate digesting the agarose.

A new hour-long incubation is performed at 37° C.

After this last incubation, the content of the wells/flasks is carefully mixed so that the agarose remains that may not have been digested are mixed with the medium, and this medium is removed from the well/flask.

Fresh culture medium is then added on the cells.

The cells are introduced in the culture oven at 37° C. and 5% $CO_2$ until the next day to allow better recovery of the transport period. After this moment, the cells will be prepared for carrying out the desired process.

The cells can optionally be extracted from the cell support in which they were cultured and transported by means of basic cell culture techniques in order to carry out the desired process.

If the cells were arranged in the agarose and agarase mixture (according to FIGS. 5b and 5c), i.e., cells embedded in the mixture, the instructions to abide by for cell recovery are the following:

After the first three steps described above, the following is carried out:

After incubation, the content of the tube is homogenized well, and a gentle centrifugation (800-1000 g) is carried out for the purpose of separating the cells from the mixture of digested agarose, medium and agarase remains and being able to recover them at the bottom of the tube.

After centrifugation, the cells are resuspended in fresh culture medium, the viable cells are counted and seeding is performed in standard culture conditions.

The cells are introduced in the culture oven at 37° C. and 5% $CO_2$ until the next day to allow better recovery of the transport period. After this moment, the cells will be prepared for carrying out the desired process.

v. Verifying Cell Integrity after the Transport Period with the System of the Invention by Means of Studying Cytotoxicity and Cell Morphology After transport and cell recovery, once the period has elapsed which allows the cells to be recovered from the entire process described, cell integrity is characterized by means of performing cytotoxicity assays and the study of cell morphology.

At least 85% intact cell viability and integrity in the transported cells is considered an optimal quality standard.

To perform this verification, proliferation and cytotoxicity assays are considered to be equivalent, assaying the proliferative capacity of the cells by means of incorporating MTT, which is a direct measurement of the metabolic capacity of the cells exposed to the transport system, such that if the exposure to the mixture is toxic for the cells their metabolism will be affected, and this will be directly reflected in a reduction of their proliferative capacity.

As is known of the state of the art, the MTT test is based on the capacity that mitochondrial enzymes of living cells have for transforming some substrates into other secondary metabolites. The amount of compound formed depends on the activity of mitochondrial dehydrogenase, which is a clear indicator of the number of viable cells existing in the culture.

As is observed in FIG. 6, it can be concluded that the transport medium does not significantly affect cell viability as modifications of the proliferation rate of the cells with respect to the control (23° C.) and the culture (37° C., 5% $CO_2$) do not occur, which indicates that the cells have not experienced cytotoxic effects during the time they were maintained in the system of the invention.

In turn, FIG. 7 shows how differences in the cell morphology of the cultures assayed in the same conditions as those described in the preceding paragraph are not observed.

In view of the aforementioned, it can be concluded that the use of the transport system described by the present invention for the transport of cell cultures neither modifies nor alters the cell viability or the cell morphology of the cell cultures transported therein.

The following specific examples provided in this patent document are to illustrate the nature of the present invention.

These examples are included only for illustrative purposes and must not be interpreted as being limitations to the invention herein claimed.

The following cell types were used to carry out the examples described in the present invention: SK-N-MC cells, MDCK-II and MDCK-II-MDR1 cells, CHO cells of murine origin, mesenchymal cells, keratinocytes and fibroblasts, the culture conditions and characteristics of which are known by a person skilled in the art.

The election of these cell types has been performed depending on the characteristics typical of each cell type due to the importance of assaying the transport system using cell types with varied characteristics proving the validity of the system with a broad range of cultures. A second election criterion was based on the final application of the transported cells, assessing the selection of cell types commonly used for identifying drugs, gene targets, etc.

Therefore, in view of the following examples it can be concluded that the agarose-agarase mixture does not affect the viability of the different cell types, so it can be determined that the transport medium can be applied to any cell type, whether the latter grow adhered to the surface of a support or, in contrast, grow in suspension in the specific culture medium.

EXAMPLES

Example 1

Determining the Ranges of Agarose and Agarase in the Transport System 1.1 Determining the Final Agarose Concentration in the System Taking into account that each of the types or cell lines requires the use of a different and specific culture medium, and that the properties of the different culture media differ from one another, and on many occasions commercially prepared culture media do not provide the information necessary for identifying the specific characteristics of the medium, it is necessary to empirically verify in each of the culture media to be transported the final agarose concentration necessary for applying the transport system of the present invention.

To determine the final agarose concentration range that will be used in the system, a low melting point agarose stock solution (Invitrogen) is prepared with a final concentration of 2% agarose in saline solution (1× PBS). Different dilutions are prepared from this solution, with a final percentage of agarose from 0.1% to 1% in the different culture media showing different characteristics.

The culture media used for these studies are DMEM medium with 10% bovine fetal serum and 1% antibiotic, Han's F12 medium supplemented with 10% bovine fetal serum and 1% antibiotic, MEM medium supplemented with 2 mM L-glutamine, 1 mM sodium pyruvate, 0.1 mM non-essential amino acids, 50 mg/ml of gentamicin and 1% antibiotic, EpiLife Medium (Cascade Biologics) supplemented with the human keratinocyte growth supplement V2 (Cascade Biologics), and 106 medium (Cascade Biologics) supplemented with the growth supplement LSGS (Cascade Biologics).

Figure 1:
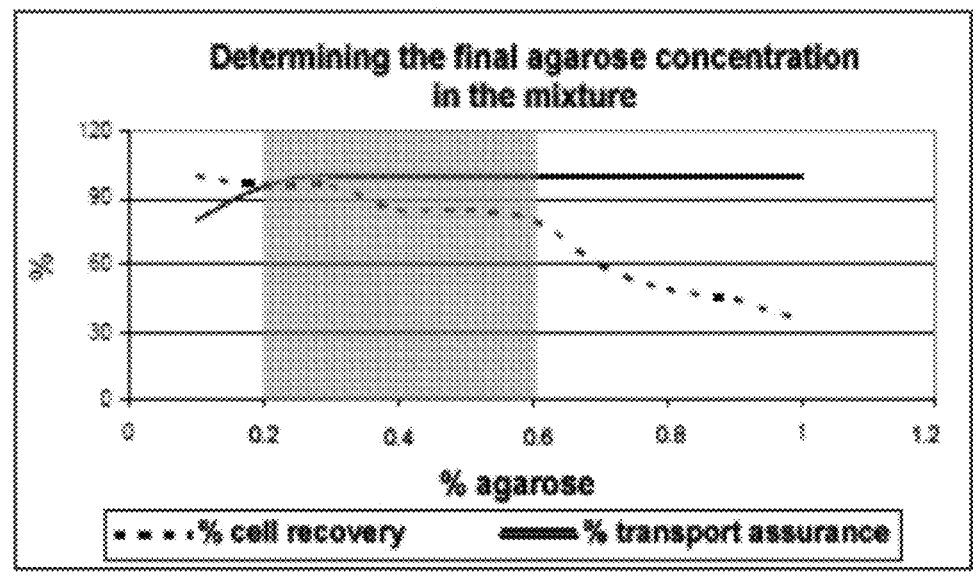
FIG. 1: Agarose concentration in the final transport mixture.

As is observed in FIG. 1, in the mixtures containing a final agarose concentration of less than 0.2%, the system does not have the desired strength and consistency which assure the reliable transport of the cells seeded in the selected support.

As described in the present invention, the objective of the system is to generate a mixture that is consistent enough for the culture to be transported in reliable conditions and the cells do not suffer due to the movements and fluctuations in the course of transport; and on the other hand, it is necessary once the culture reaches its destination for the cells to be able to be recovered for their use (either by an experienced user or by users who are not familiar with cell culture techniques and methodology) in a simple and easy manner with an optimal recovery percentage. To that end, the percentage of agarose in the mixture established as optimal was that percentage in which the mixture was strong enough for the cells to be transported without the support experiencing any type of sliding, but which at the same time allows being separated from the culture in an easy and efficient manner.

Therefore, the final percentage of agarose in the mixture must be greater than 0.2% regardless of the culture medium used for preparing the mixture.

TABLE 1

Optimal ranges of the final % of agarose in the mixture
depending on the culture medium used in the invention.

| Culture medium | Final % of agarose in the mixture |
|---|---|
| Supplemented MEM + 10% bovine fetal serum + 1% antibiotic | 0.3-0.4 |
| Ham's F12 + 10% bovine fetal serum + 1% antibiotic | 0.5 |
| DMEM + 10% bovine fetal serum + 1% antibiotic | 0.3-0.4 |
| MesenPro + 1% antibiotic | 0.6 |
| 106 Medium + 1% antibiotic | 0.5-0.6 |
| EpiLife Medium + 1% antibiotic | 0.5-0.6 |

After the concentration of 0.2%, and in all the concentrations greater than 0.3%, the mixture has an ideal consistency for transport. The maximum concentration of 1% agarose shows a completely solid consistency which reliably assures cell transport.

However, despite the fact that the greater the agarose concentration used in the final mixture for transport the more reliable said transport is, it is also necessary to take into account the features of the system of the invention, which relates to the simple and easy recovery of the cell culture after its transport. Therefore, the greater the agarose concentration in the final mixture, the more difficult it will also be in the moment of recovering the culture due to its high rigidity.

In this sense, the different percentages of agarose in the mixture have been assayed with the different culture media from 0.3% to 1% (FIG. 1) to determine the greatest optimal concentration for the system. After verifying the degree of solidification of the mixture for each media, it has been established that the upper limit of agarose concentration to be used in the system is 0.6%.

If the final agarose concentration in the mixture is greater than the optimal recommended concentration, the recovery of the cells forming the transported culture will be difficult, decreasing the cell recovery yield and preventing complete removal of the mixture from the culture.

Therefore, the agarose concentration range in the final transport mixture is 0.2-0.6%, preferably 0.5%, in the culture medium based on a more concentrated agarose solution prepared at 2% in saline solution (1× PBS) and subsequently sterilized.

1.2. Final Agarase Concentration in the System

Figure 2:
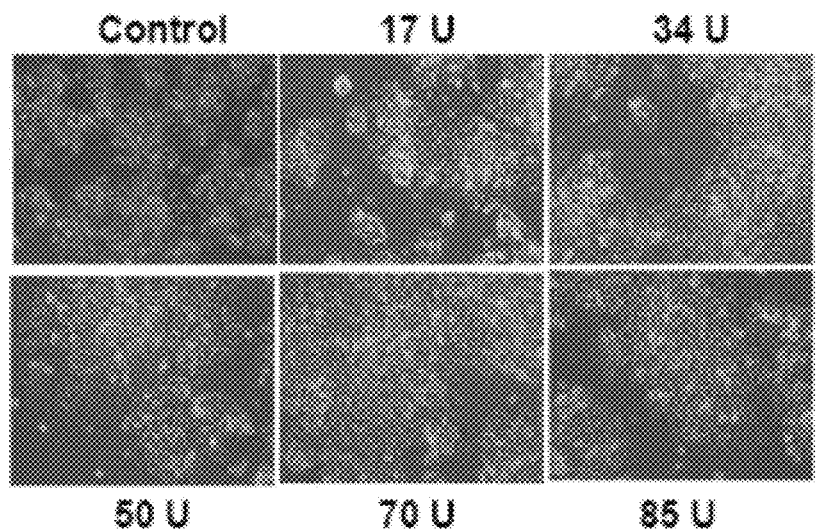
FIG. 2: Determination of the final agarase concentration in the system by means of analyzing the cell morphology of the culture after its exposure to the agarose and agarase mixture The images of FIG. 2 show the cell morphology of the culture of the SK-N-MC cells after its exposure to the transport medium (agarose-agarase mixture) using different concentrations of the latter for the purpose of determining the effect of each of the assayed concentrations on cell morphology. The cells appearing in the images have been exposed during the estimated transport time (24 hours) with the mixture of 0.3% agarose and medium specific for this cell type, and with the agarase concentrations indicated in each case. After incubating with the transport medium, cell recovery has been carried out according to the process described in the present document and after 24 hours in culture (37° C., 5% $CO_2$), the integrity and morphology of the culture have been analyzed by means of microscopy.

To determine the percentage of agarase used in the agarose mixture, the amount of agarase necessary for obtaining the final percentage established has been mixed with different amounts of agarase to achieving final agarase concentration range of 80 units per 1 ml of 1% agarose. Determining the final agarase concentration in the mixture was based on the visual observation of the strength of the mixture and on the microscopic observation of cell integrity and morphology (FIGS. 2 and 7).

One of the considerations when determining the percentage of agarase with which to prepare the transport medium is the consistency of the mixture of agarose with agarase and its corresponding volume of specific culture medium.

In order for the cells to be reliably transported by means of the system of the present invention, it is necessary for the agarose-agarase mixture to be strong enough to protect the cells during the process. It is therefore necessary for the agarose-agarase mixture to show a consistency which assures the desired conditions and at the same time, it is necessary to verify that cell integrity and morphology is maintained after contact with the agarose and agarase mixture.

From the concentration of 90 units of agarase per milliliter of 1% agarose, the agarose-agarase mixture does not show the consistency necessary for assuring optimal cell transport because the transport mixture shows a consistency that is too liquefied for carrying out reliable transport.

Therefore, the agarase concentration of the final agarose and agarase mixture in the system will preferably be 80 units of agarase per milliliter of 1% agarose.

As shown in FIG. 2, cell integrity and morphology of the cultures exposed to the agarose mixture with the different final agarase concentrations show no difference with respect to the cultures that have been exposed to said mixture. Not even the cells in contact with the highest agarase concentration (85 units of agarase per milliliter of 1% agarose) show a difference in cell viability or morphology.

Example 2

Assays Carried out to Validate the System Described in the Invention 2.1.—Characterizing Cell Integrity after Exposure to the Mixture of Agarose with Agarase and Medium by Means of Cytotoxicity Assays Depending on the selected cell type, the cells are seeded in the appropriate density and media and the plate(s) are cultured at 37° C. and 5% $CO_2$.

The culture surfaces can optionally be treated with poly-L-lysine, as described below, prior to seeding the cells:

The poly-L-lysine stock solution is at a concentration of 500 μg/ml and sterile by filtration. The final poly-L-lysine concentration selected is 60 μg/ml. To prepare the solution to be added in the wells, the suitable volume of poly-L-lysine stock solution is prepared in $H_2O$ to obtain the desired concentration in treating the culture surface.

80 μl of the suitable solution are added in the wells of the 96-well plate and the plates are incubated at room temperature, uncovered without the lid inside the laminar flow cabinet operating for 1 hour.

After the incubation, each of the wells is washed 3 times with a tempered saline solution (1× PBS). The plates are covered with their corresponding lids and are exposed to ultraviolet radiation (UV) for a time period of at least 1 hour to allow sterilizing the culture surfaces.

These plates are used within the first week after they are prepared.

Seeding the Cells

The SK-N-MC cells are seeded at a density of 40,000 cells per well in 200 μl of medium in each well of the 96-well plate. These cells are cultured in MEM medium supplemented with 2 mM L-glutamine, 1 mM sodium pyruvate, 0.1 mM non-essential amino acids, 50 mg/ml of gentamicin and 1% antibiotic.

In turn, CHO cells are seeded at a density of 20,000 cells per well in 200 ul of medium in each well of the 96-well plate. The culture medium of the CHO cells consists of Han's F12 medium supplemented with 10% bovine fetal serum and 1% antibiotic.

The seeding density that is used for the MDCK-II and MDCK-II-MDR1 cell lines is 15,000 cells and 200 μl of medium per well of the 96-well plate. The medium specific for culturing these cells is DMEM medium supplemented with 10% bovine fetal serum and 1% antibiotic.

The human mesenchymal cells are seeded at a density of 5,000 cells per well of the 96-well plate in 200 μl. The specific culture medium in which these cells are cultured is the MesenPro medium (Gibco). MesenPro medium is a medium with reduced serum content (2%) and is especially formulated for the growth of mesenchymal cells.

Adult human keratinocytes are cultured at a cell density of 10,000 cells in 200 µl of medium per well of the 96-well plate. In this case the medium used for cell growth consists of EpiLife Medium (Cascade Biologics) supplemented with human keratinocyte growth supplement V2 (Cascade Biologics) which contains a recombinant human insulin-like growth factor (ILGF), recombinant human epidermal growth factor, prostaglandin E-2 and hydrocortisone.

The number of cells seeded in the case of the fibroblasts is 5,000 cells per well of 96-well plate in 200 µl of medium. The medium used for culturing fibroblasts consists of 106 medium (Cascade Biologics) supplemented with the LSGS growth supplement (Cascade Biologics) containing fetal bovine serum, hydrocortisone, human epidermal growth factor, basic growth factor for fibroblasts and heparin.

The next day the plate is removed from the incubator and placed on a cooled surface, for example a box with ice, and in sterile conditions the different cultures are covered with the transport medium of the invention which is prepared as described below:

Preparing the Transport Medium

The 2% agarose solution prepared in 1× PBS is melted in a microwave, the suitable volume is taken to prepare a solution with a final agarose concentration of 0.3% in the culture medium specific for each cell culture. The agarase, which is prepared at a concentration of 0.2-2 mg/ml (255.6-2,556 U/ml) in potassium phosphate buffer pH 6.0 or 1× PBS, and the final concentration of which in the mixture will be of 60-80 units of agarase per milliliter of 1% agarose, i.e., 18 U/ml for the concentration of 0.3% used, is added to the agarose solution. 150 µl of 2% agarose and 7-95 µl of agarase at 0.2-2 mg/ml (255.6-2,556 U/ml) are added for each ml of transport medium.

Adding the Transport Medium on the Cell Culture

Once the transport medium is mixed well and tempered at 37° C., the volume of medium is removed from the wells of the 96-well plate in which the mixture is being added, covering the cell culture.

Therefore, 150 µl of the mixture are added on the cells seeded in each of the wells and the plate is maintained on ice until the mixture acquires the desired consistency, approximately 15-30 minutes after it is added to the plate.

Preparing the Plate for Transport and Transport Conditions

The plate is then completely sealed with parafilm and is maintained at the transport temperature, 18-23° C., preferably 22° C.

Receiving the Plate, Removing the Transport Medium

After the transport period necessary for reaching its destination, in this case 24 hours of transport have been assayed, the plate must be carefully unwrapped and its surface disinfected with EtOH before being introduced in the cell culture incubator at 37° C. to begin digesting the agarose-agarase covering and the subsequent cell recovery.

Therefore, the plate is introduced in an incubator at 37° C. and 5% $CO_2$. The incubation in these conditions must be for approximately 2 hours. Once the two hours of the first incubation have elapsed, the plate is taken out of the incubator and 100 µl of cell culture medium tempered at 37° C. are added to each of the wells, and the plate is returned to the incubator for another hour.

The agarose plus agarase covering is removed after the last hour of incubation. The content of the well is mixed very gently and carefully with the aid of a P100 or P200 pipette, and the culture medium mixed with culture medium is removed carefully so as to not entrain and lift the cells which are adhered to the bottom of the well. Tempered fresh medium is then added. At this point, it is necessary to try to remove the maximum amount of medium with agarose, but without risking the culture.

Once all the wells of the plate are completed, when they all contain fresh medium, the plate is returned to the incubator until the next day to allow the cells to recover after the transport and cell recovery processes.

Proliferation Assay

Once the recovery period has elapsed, the cells are ready to carry out the relevant assays, in this specific case a proliferation assay. Parallel to determining the proliferative capacity of the cells maintained with the agarose and agarase mixture in the previously described conditions, a way to control the proliferative capacity of all the cell lines and primary cultures that have been maintained in the following conditions is also assayed:

Culture: the same cell lines and primary cultures that were exposed to the agarose and agarase mixture but incubated in normal culture conditions (37° C., 5% $CO_2$), and for which the proliferation rate will be that considered as the reference control.

Control: the same cell lines and primary cultures that were exposed to the agarose and agarase mixture and that were maintained in the same temperature conditions, packaging conditions, etc., as those exposed to the mixture but have only been in contact with their specific culture medium. These cells are called Control in the graphs of FIG. 6, showing the cell proliferation of these assays. The objective of including this control in the assay consists of determining the effect of the transport conditions (temperature, packaging, time, . . . ) on cell viability and proliferation; determining if the effects of the transport are due to the contact with the mixture, or in contrast with the conditions in which they are transported.

Cell integrity was determined by means of measuring cell proliferation by means of the MTT test.

The MTT test is based on the capacity that mitochondrial enzymes of living cells have for transforming some substrates into other secondary metabolites. The amount of compound formed depends on the activity of mitochondrial dehydrogenase, which is a clear indicator of the number of viable cells existing in the culture.

Specifically, in this mitochondrial test, Cell Proliferation kit I (MTT), Cat. No. 1 465 007 Roche, the transformation carried out by cellular mitochondrial succinate dehydrogenases of tetrazolium salt (yellow) to insoluble formazan crystals (blue) is determined. The cells are subsequently permeabilized and the formed crystals are solubilized, giving way to a colored solution that can be quantified by measuring its absorbance in an ELISA microplate reader at a wavelength of 550 nm.

The process to abide by is the following:

In the moment in which the proliferative capacity or cell integrity is to be assayed, 10 µl of the MTT solution (0.5 mg/ml) are added to the culture to each well per 100 µl of medium, and it is incubated for 4 hours at 37° C. in the incubator.

When the incubation ends, the formazan crystals can be observed inside the cells. 100 µl of the solubilizing solution are added to each culture or well and it is incubated at 37° C. in the incubator overnight. The cells are thus permeabilized and the crystals are solubilized, giving way to a readily quantifiable colored solution.

Once the crystals are solubilized, the culture plate is read directly with an ELISA multiplate reader at 550 nm. Before reading, it is advisable to clean the lower surface of the plate with ethanol.

The mitochondrial activity was read after the recovery period of the cells at time 0, 24 and 72 hours. FIG. 6 shows the representation of the absorbance values over time obtained from measuring the proliferation by the MTT method in all the cell types and primary cultures assayed.

The analysis of the proliferation rate of the SK-N-MC, CHO, MDCK-II and MDCK-II-MDR1 cell lines depicted in FIG. 6 shows no negative effect whatsoever on cell growth of these cell types assayed with the medium and conditions defined for cell transport, even showing an increase in the proliferation rate of these cells after exposure to the mixture and conditions determined for cell transport.

After analyzing the growth of the primary cultures of the mesenchymal cells (AMSC), keratinocytes and fibroblasts, also shown in FIG. 6, it is observed that the exposure of these cells to the agarose-agarase mixture and their maintenance in the selected transport conditions does not significantly affect their proliferation rate. In these cases a slight increase of the proliferative capacity of the cultures exposed to the mixture is also observed.

From these results it is concluded that the transport medium (agarose-agarase) does not significantly affect cell integrity because the proliferation rate of the cells exposed to the mixture and transport conditions is similar to that of the cells not exposed to it and to those cultured under the same temperature conditions (23° C.). It can therefore be concluded that the cell cultures exposed to the medium and transport conditions, furthermore proliferate in a manner similar to the cells maintained in standard culture conditions (37° C., 5% $CO_2$).

Therefore, a particular embodiment of the invention corresponds to a final percentage of 0.3% of agarose, 80 units of agarase per milliliter of 1% agarose of the mixture of the system and the specific temperature conditions (22° C.) for transport do not affect the integrity of the cells assayed in the conditions described.

2.2 Characterizing Cell Integrity after Exposure to the Mixture of Agarose with Agarase and Medium by Means of Morphological Verification of the Cell Culture Seeding the Cells The cells are seeded in a 24-well plate at a different cell density depending on the cell type involved, and these cells will be cultured in the specific culture medium for each cell type as described in the previous assay.

For the specific embodiment of this particular assay, the cells were seeded with their specific culture medium at 37° C. and 5% $CO_2$ at the following densities: SK-N-MC 300,000 cells per well in 1 ml; CHO 100,000 cells per well in 1 ml of medium; MDCK-II and MDCK-II-MDR1 65,000 cells per well in 1 ml of medium; human mesenchymal cells 50,000 cells per well in 1 ml of medium; adult human keratinocytes at 110,000 cells per well in 1 ml of medium; fibroblasts 90,000 cells per well in 1 ml of medium.

The cell cultures are treated with a transport medium as described in the previous example.

Once the transport medium has been removed from the cells and they have been recovered as described in the previous example, the cell morphology of the culture of each of the cell lines and primary cultures included in the assay is analyzed. Parallel to the analysis of the cell morphology by means of microscopy of the cells maintained with the transport mixture, a way to control the cell morphology of all the cell lines and primary cultures in the same conditions (culture and control) that were used in the previous example is also analyzed.

Cell morphology is analyzed by means of microscopic observation of the cell cultures of the SK-N-MC neuroblastoma cells, CHO cells, MDCK-II and MDCK-II-MDR1 cells, and also the primary cultures of mesenchymal cells, fibroblasts and keratinocytes, all of a human origin.

The analysis was performed during the entire cell manipulation process. FIG. 7 shows the images obtained from this morphological analysis. FIG. 7a shows the appearance of the culture of all the cells assayed before incorporating the mixture of agarose with agarase and medium. The normal appearance of each of the cell types can be observed therein.

FIG. 7b shows the appearance of each of the cultures in the moment prior to removing the mixture of agarose with agarase and medium. In other words, the cells appearing in these images are coated with the agarose and agarase mixture in the moment the image is captured. The control corresponds to the cells that remained in the same plate as the cells exposed to the mixture of agarose with agarase and medium, maintained in the same conditions as the cells with the mixture, but which, however, have had no contact whatsoever with the assayed mixture. It can be observed in the images corresponding to this point that there is no difference whatsoever in the cell morphology of the cultures maintained at 23° C., without an external supply of $CO_2$ and in the packaging conditions, if they were in contact with the transport medium and if they were only maintained with their specific culture medium, when it is compared with the morphology of the cells maintained in standard culture conditions (37° C., 5% $CO_2$).

Figure 7C:
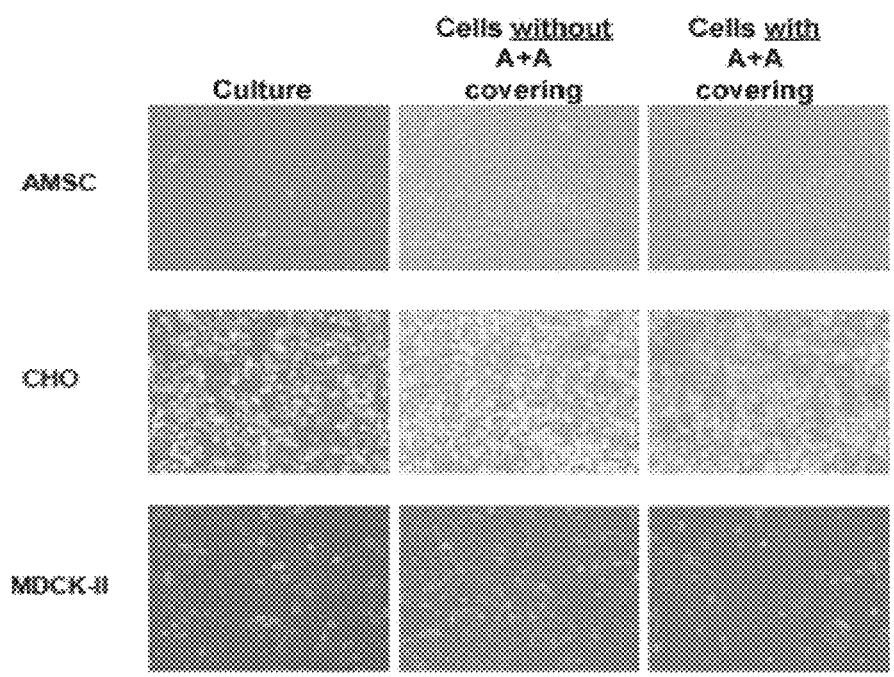

FIG. 7c shows the images corresponding to the cell cultures the day after removing the mixture of agarose plus agarase and medium after the recommended recovery period for the cells. FIG. 7c shows the images of the normal morphology of all these cell lines and primary cultures in normal culture conditions (control cells that were maintained in culture in the usual manner), and they are depicted in FIG. 7c as Culture. Furthermore, FIG. 7c shows the images of the morphological analysis of the cells called Control maintained in the transport conditions together with those assayed with the mixture of agarose plus agarase and medium, but without contact with the mixture. This figure finally shows the morphology corresponding to the cell cultures of all the cells that were treated and exposed to the mixture of agarose plus agarase and medium in the conditions described in the methodology, called Agarose+agarase.

It can be determined from these images that no differences are observed in the cell morphology of the cultures assayed in the transport conditions called culture, control and agarose+agarase. Therefore, it can be concluded that applying the mixture of agarose plus agarase and medium in the determined conditions neither modifies nor alters the normal cell morphology of the cultures of the SK-N-MC neuroblastoma cells, CHO cells, MDCK-II and MDCK-II-MDR1 cells, and also the primary cultures of mesenchymal cells, fibroblasts and keratinocytes, all of a human origin.

2.3 Characterizing the Increase of the Capacity of Cell Adherence of the SK-N-MC Cells on Plates Treated with Laminin by Means of Proliferation Assay with MTT and Verification of the Morphology and Cell Density by Microscopy Of all the adherent cell lines selected for the transport assay with the system of the present invention, the epithelial neuronal SK-N-MC cells had the lowest capacity of adherence. Therefore, the SK-N-MC cells were selected for the assay of the system in plates specifically treated to increase cell adherence.

Several scientific literature references describe laminin as the component of the extracellular matrix that is most commonly used to increase the adherence of the neuronal cells, as is the case of the SK-N-MC cells (10).

As a result, SK-N-MC cells were cultured in standard 24-well plates and in 24-well plates previously treated with laminin (Laminin 24-well Multiwell plates, BD) at a cell density of 300,000 cells per well and 1 ml of specific medium consisting of MEM medium supplemented with 2 mM L-glutamine, 1 mM sodium pyruvate, 0.1 mM non-essential amino acids, 50 mg/ml of gentamicin and 1% antibiotic at 37° C. and 5% $CO_2$.

The day after seeding the SK-N-MC cells in the standard 24-well plates and in 24-well plates treated with laminin, transport conditions are simulated according to the specifications described in the previous example.

Once the time necessary for the cells to recover from transport has elapsed, the proliferation rate of both cultures is determined by means of measuring cell proliferation at times 24 and 48 h using the MTT test described in the previous example.

FIG. 8*a* shows the depiction of the absorbance values over time obtained from measuring the proliferation by the MTT method in the cells cultured in the usual manner and those cultured on the surface treated with laminin.

The analysis of the proliferation rate of the SK-N-MC cells depicted in FIG. 8*a* shows an increase in the proliferation of the cells of the plate treated with laminin after 24 hours in culture due to the fact that covering with laminin provides the SK-N-MC cells with greater adhesion to the substrate of the support, allowing the establishment of a larger number of cells and therefore increasing the number of viable cells in the culture. After 48 hours in culture, the proliferation rate of both cultures is equal; however, in the images of the cell cultures (FIG. 8*b*) a greater cell density is still observed in the culture plates with laminin.

In turn, the analysis of the cell morphology of the cultures of SK-N-MC in normal 24-well plates and 24-well plates treated with laminin shown in FIG. 8*b* proves that the number of cells in the culture in plates with laminin is greater than that of the culture in a normal plate despite the fact that the number of starting cells for both of them is the same, which reaffirms the results obtained from measuring the proliferation by means of MTT. The non-detection of the difference in the cell density by the proliferation assay by means of MTT can be due to the high cell confluence of both cultures.

Therefore, it can be concluded that the plates treated with laminin maintain the cell morphology of the starting culture and favor cell adhesion to the substrate, promoted by treatment the support with laminin.

2.4. Characterizing the Increase of the Capacity of Cell Adherence of the SK-N-MC Cells on Plates Treated with poly-L-lysine by Means of a Proliferation Assay with MTT and Verification of the Morphology and Cell Density by Microscopy 2.4.1 Assaying Cell Integrity of the Transport System after Increasing Exposures of Poly-L-Lysine and Determining the poly-L-lysine Concentration Ranges in the Transport System.

Treating the Culture Surfaces with poly-L-lysine

The poly-L-lysine stock solution is at a concentration of 500 µg/ml, sterile by filtration. The final poly-L-lysine concentrations assayed with the SK-N-MC cells were between 10-200 µg/ml.

After defining the poly-L-lysine concentrations to be used in the assay, the amount of poly-L-lysine to be added in each case is determined so that the final concentration complies with the desired concentration.

80 µl of the suitable solution are added to the wells of the 96-well plate and the plates are incubated at room temperature, uncovered without the lid inside the laminar flow cabinet for 1 hour.

After incubation, each of the wells is washed 3 times with a tempered saline solution (1× PBS). The plates are covered with their corresponding lids and are exposed to ultraviolet radiation (UV) for a time period of at least 1 hour to allow sterilizing the culture surfaces.

These plates are used within the first week after they are prepared.

Seeding the SK-N-MC Cells in the Plates Treated with poly-L-lysine

The SK-N-MC cells are seeded in the plates treated with poly-L-lysine at a density of 15,000 cells per well in 200 µl of medium in each well of the 96-well plate. These cells are cultured in MEM medium supplemented with 2 mM L-glutamine, 1 mM sodium pyruvate, 0.1 mM non-essential amino acids, 50 mg/ml of gentamicin and 1% antibiotic.

Assaying Cell Integrity after Exposure to Increasing poly-L-lysine Concentrations Cell integrity was determined by means of measuring the cell proliferation by means of the MTT test.

After a brief (4 hours approximately) exposure of the cells to the surface of the plate, the first cell integrity measurement is taken, with its corresponding addition of MTT to determine the initial value or time 0 hours.

The MTT test is based on the capacity that mitochondrial enzymes of living cells have for transforming some substrates into other secondary metabolites. The amount of compound formed depends on the activity of mitochondrial dehydrogenase, which is a clear indicator of the number of viable cells existing in the culture.

Specifically in this mitochondrial test, Cell Proliferation kit I (MTT) Cat. No. 1 465 007 Roche, the transformation carried out by cellular mitochondrial succinate dehydrogenases of tetrazolium salt to insoluble formazan crystals is determined. The cells are subsequently permeabilized and the formed crystals are solubilized, giving way to a colored solution that can be quantified by measuring its absorbance in an ELISA microplate reader at a wavelength of 550 nm.

The process to abide by is the following:

1. In the moment in which the proliferative capacity or cell integrity is to be assayed, 10 1.11 of the MTT solution (0.5 mg/ml) are added to the culture to each well per 100 µl of medium, and it is incubated for 4 hours at 37° C. in the incubator.
2. When the incubation ends, the formazan crystals can be observed inside the cells. 100 µl of the solubilizing solution are added to each culture or well and it is incubated at 37° C. in the incubator overnight. The cells are thus permeabilized and the crystals are solubilized, giving way to a readily quantifiable colored solution.
3. Once the crystals are solubilized, the culture plate is read directly with an ELISA multiplate reader at 550 nm. Before reading, it is advisable to clean the lower surface of the plate with ethanol.

Poly-L-lysine Concentration in the Transport System

The graphs of FIG. 10 show the cytotoxicity curves of the SK-N-MC cells after contact with the surface treated with poly-L-lysine at different concentrations.

FIG. 10*a* shows the upper poly-L-lysine concentration range (100-200 µg/ml) assayed. In contrast, FIG. 10*b* shows the lower poly-L-lysine concentrations (10-75 µg/ml) assayed.

As can be observed in graph 10a, the increasing poly-L-lysine concentrations show a reduction in the proliferative capacity of the SK-N-MC cells. In FIG. 10b, it is observed that the cultures exposed to the lower poly-L-lysine concentrations show a proliferation kinetics that is virtually unchanged with respect to that observed in the cells not exposed to the poly-L-lysine.

From the previous assay, it can be deduced that despite the fact that none of the concentrations dramatically affects the integrity or proliferative capacity of the culture, from the poly-L-lysine concentration of 75 µg/ml, cell proliferation seems to be reduced at 72 hours. Therefore, the poly-L-lysine concentration range in the transport system is 10-75 µg/ml, preferably 50-70 µg/ml, considering the final preferred concentration of 60 µg/ml.

2.4.2 Characterizing Cell Integrity after the Contact with the Surfaces Treated with Different poly-L-lysine Concentrations by Means of Morphological Verification of the Cell Culture Treating the Culture Surfaces with poly-L-lysine The poly-L-lysine stock solution is at a concentration of 500 µg/ml, sterile by filtration. The final poly-L-lysine concentrations assayed with the SK-N-MC cells were between 10-50 µg/ml.

After defining the poly-L-lysine concentrations to be used in the assay, the amount of poly-L-lysine to be added in each case is determined so that the final concentration complies with the desired concentration.

300 µl of the suitable solution are added to the wells of the 24-well plate and the plates are incubated at room temperature, uncovered without the lid inside the laminar flow cabinet during 1 hour.

After incubation, each of the wells is washed 3 times with a tempered saline solution (1× PBS). The plates are covered with their corresponding lids and are exposed to ultraviolet radiation (UV) for a time period of at least 1 hour to allow sterilizing the culture surfaces.

These plates are used within the first week after they are prepared.

Seeding the Cells

The cells are seeded in a 24-well plate at a different cell density depending on the cell type involved, and these cells will be cultured in the specific culture medium for each cell type as described in previous examples.

For the specific embodiment of this particular embodiment, the cells were seeded with their specific culture medium at 37° C. and 5% $CO_2$ at the following densities: SK-N-MC 150,000 cells per well in 1 ml; MDCK-II-MDR1 65,000 cells per well in 1 ml of medium; human mesenchymal cells 50,000 cells per well in 1 ml of medium; human articular chondrocytes 65,000 cells per well in 1 ml of medium.

Analyzing the Cell Morphology of the Cultures Exposed to poly-L-lysine

Once the cells have been seeded in the culture surface treated with poly-L-lysine, the cell morphology of the culture of each of the cell lines and primary cultures included in the assay is analyzed. Parallel to the analysis of the cell morphology by means of microscopy of the cells exposed to poly-L-lysine, a way to control the cell morphology of all the cell lines and primary cultures in the non-treated culture surface (control) is also analyzed.

Cell morphology is analyzed by means of microscopic observation of the cell cultures of the SK-N-MC neuroblastoma and MDCK-II-MDR1 cells, and also the primary cultures of mesenchymal cells and articular chondrocytes, all of a human origin, during the 24, 48 and 96 hours after exposure to the culture surface treated with poly-L-lysine.

FIG. 11 shows the appearance of each of the cultures used during the exposure to poly-L-lysine. The control corresponds to the cells that were cultured in plates without treatment and maintained in the same conditions as the cells in contact with poly-L-lysine, but which, however, have had no contact whatsoever with the assayed molecule. The analysis was carried out during 96 hours. It is observed in the images corresponding to this assay that there is no difference whatsoever in the cell morphology of the cultures exposed to poly-L-lysine with respect to the morphology of the cells not exposed to contact with said molecule.

FIG. 11a shows the images corresponding to the cultures of the SK-N-MC cells; FIG. 11b shows the MDCK-II-MDR1 cells; the cells appearing in FIG. 11c are human mesenchymal cells; and finally, the morphology of human articular chondrocytes can be observed in FIG. 11d.

It can be determined from these images that no differences are observed in the cell morphology of the cultures assayed after their contact with poly-L-lysine. Therefore, it can be concluded that contact with the treated surfaces neither modifies nor alters the normal cell morphology of the cultures of the SK-N-MC neuroblastoma cells, MDCK-II-MDR1 cells, and also the primary cultures of mesenchymal cells and chondrocytes, all of a human origin.

Example 3

Cell Transport in a 96-Well Plate for Drug Screening

The SK-N-MC cells are seeded in 96-well plates at a density of 40,000 cells per well in 200 µl of medium. These cells are cultured in their specific medium consisting of MEM medium supplemented with 2 mM L-glutamine, 1 sodium pyruvate, 0.1 mM non-essential amino acids, 50 mg/ml of gentamicin and 1% antibiotic. They are cultured at 37° C. and 5% $CO_2$.

The day after seeding, the covering of the transport medium is applied and the transport conditions of the plate are simulated as described in the previous examples.

Once the recovery period of the transported cells has elapsed, said cells are ready to be treated with different molecules or drugs and can analyze if these compounds have an effect on cell proliferation, or cytotoxicity of the cells seeded in said plate by the MTT test, described in previous examples.

Example 4

Transport of AMSC Cells in a 12-well Plate for Analyzing Membrane Marker Expression in Cell Differentiation Processes The AMSC cells are seeded in 12-well plates at a density of 80,000 cells per well and are cultured with the special Mesen-Pro culture medium at 37° C. and 5% $CO_2$.

The day after seeding the covering of the transport medium is applied with an agarose concentration of 0.5% and the final agarase concentration of 30 U/ml, which is prepared according to that described in Example 2 and the transport conditions of the plate are simulated as described in the previous examples.

Once the recovery period has elapsed, the mesenchymal cells are subjected to the treatment specific for inducing adipogenesis, which promotes cell differentiation. After the estimated treatment and time, the specific markers will be analyzed and the differentiation studied.

The process for inducing adipogenesis in the mesenchymal cells transported by the system of the invention comprises the following steps:

- The cells are maintained in culture with the MesenPro Growth Medium during the time necessary for the formation of the monolayer.
- Once the monolayer is formed, the specific differentiation (adipogenic) medium consisting of MesenPro growth medium supplemented with 0.5 mM isobutyl methylxanthine, 1 µM dexamethasone, 10 µg/ml of insulin (Sigma 1-2767), 200µ of indomethacin and 1% antibiotic is applied to the culture. The medium is changed every 3-4 days.
- After the third treatment with the adipogenic differentiation medium, lipid vacuoles begin to form within the treated mesenchymal cells. These vacuoles are detected by means of Oil-red-O staining.

Therefore, after the period of incubation of the mesenchymal cells with the differentiating medium specific for inducing adipogenesis, the specific markers are analyzed and the differentiation of the mesenchymal cells into adipocytes is studied.

The process of labeling with Oil-red-O consists of:
- Carefully removing the medium from each of the wells so as to not entrain the cells.
- Fixing the cells with a 4% paraformaldehyde solution during 40 minutes at room temperature.
- Carefully aspirating the fixing solution and washing the cells 3 times with 1× PBS (5 minutes per washing).
- Aspirating the 1× PBS and rinsing the cells 2 times with distilled water.
- Aspirating the water and adding to each well the sufficient amount of a 2% Oil-red-O solution (500 µl-1 ml per well) and incubating during 50 minutes at room temperature.
- After the 50 minutes have elapsed, removing the Oil-red-O from the wells with the cells and washing the cells 3 times with 1 ml of water.
- Staining the cell nuclei with a hematoxylin solution (500 µl) from 5 to 15 minutes at room temperature.
- Analyzing the presence of the lipid vacuoles under a microscope. The adipocytes have red oil drops or clusters as a consequence of the Oil-red-O dye, whereas the cell nuclei will be stained black or blue due to the hematoxylin.

Example 5

Transport of CHO Cells in a Tube for Analyzing Gene Expression

For transport in a tube, it is not necessary to seed the cells on any support, plate, flask, culture chamber or of another type, but rather the transport medium (agarose-agarase) is prepared directly.

The medium in which the CHO cells are cultured is Ham's F12 medium supplemented with 10% fetal bovine serum and 1% antibiotic.

The 2% agarose solution prepared in 1× PBS is melted in a microwave and the suitable volume is taken to prepare a solution with a final agarose concentration of 0.4%, and it is mixed with Ham's F12 medium. After the agarose, the agarase, which is prepared at a concentration of 0.2-2 mg/ml (255.6-2556 U/ml) in potassium phosphate buffer pH 6.0, and the final concentration of which in the mixture will be 24 U/ml, is added; the content of the tube is mixed well, tempering it at 37° C. and next a small volume of medium containing $0.5-1 \times 10^6$ CHO cells per ml of the mixture is added.

Next, the tube is taken to a container with ice until the mixture acquires the desired consistency, which will occur after 15-30 minutes of incubation in ice. The tube is sealed with parafilm and is sent for transport.

Once the tube is at the destination, it must be carefully unwrapped and disinfected with a small amount of 70% EtOH before continuing with its handling.

To begin the digestion of the transport medium and the subsequent cell recovery, the tube must be introduced in an oven or incubator at 37-40° C. Incubation in these conditions takes approximately 2 hours. Once the two hours of the first incubation have elapsed, the tube is taken out of the oven or incubator and 1 ml of medium or PBS (1×) tempered at 37° C. is added on the volume of each tube, and the content of the tube is mixed with the aid of a P1000 pipette in order to stir the agarose residues that may still not be digested. The tube is returned to the oven or incubator at 37-40° C. for another hour to allow the complete digestion of the agarose by the agarase of the mixture.

After the last hour of incubation, the tube is removed from the oven or incubator of 37-40° C. and its content is mixed with the aid of a P1000 pipette. The samples are subjected to a gentle centrifugation (800-1000 g) in the same tube in which the delivery was made, and the supernatant resulting from centrifugation is removed. The resulting pellet containing the CHO cells is washed with 1-2 ml of cold 1× PBS (4° C.) and after another centrifugation, the cell pellet is obtained, clean and ready for TRIZOL, a reagent selected for extracting nucleic acids, to be added to it.

Trizol LS is a single-phase solution of phenol and guanidine isothiocyanate used for extracting RNA. During homogenization or lysis of the samples, Trizol LS causes cell disruption and dissolves the cell components, maintaining the integrity of the RNA. The addition of chloroform followed by centrifugation separates the solution into an upper aqueous phase and into a lower organic phase. The RNA remains exclusively in the aqueous phase. The isolated total RNA is free of contamination with DNA and proteins.

The process for isolating RNA by means of TRIZOL is the following:
- Obtain a cell pellet by centrifugation. Discard the supernatant and completely remove the liquid residues with a pipette. Add in the fume hood 750 µl of Trizol for each $5\text{-}10.10^6$ cells. Transfer to a microtube and lyse the cells with Trizol by repeatedly pipetting. At this point the samples can be stored at −80° C.
- Incubate the samples during 5 minutes at RT to allow the complete dissociation of the nucleoprotein complexes. Add 200 µl of chloroform in the fume hood per 750 µl of Trizol added. Vigorously shake the tubes during 15 seconds and incubate them for 15 minutes at RT.
- Centrifuge the samples in a microcentrifuge at 12000 g for 15 minutes at 4° C.
- After centrifugation, different phases will be observed: the RNA remains exclusively in the upper aqueous phase. The volume of this phase must be approximately 75% of the volume of Trizol used to perform cell lysis.
- In a fume hood, transfer the aqueous phase to another microtube and precipitate the RNA by adding 500 µl of isopropyl alcohol per 750 µl of Trizol used. Mix and incubate for 10 minutes at RT. After this time has elapsed, centrifuge at 12000 g for 10 minutes at 4° C. After centrifugation, an RNA precipitate or pellet will be observed in the bottom of the microtube.

Remove the supernatant by turning the microtube over and wash the RNA pellet with 75% ethanol in DEPC-treated H$_2$O. Homogenize and centrifuge the samples at 7500 g for 5 minutes at 4° C.

Discard the ethanol by tipping the tube over once; it is important to completely remove the ethanol because if residues are left behind, they can interfere in subsequent reactions, such as PCR. Remove the ethanol residues left in the bottom of the microtube with a 10 µl pipette. Once the ethanol is completely removed, dry the RNA pellet during at least 20 minutes in ice. Do not allow the pellet to dry completely because this would hinder its solubility and partially dissolved RNA has absorbance ratios A$_{260}$/A$_{280}$<1.6. Dissolve in 12 µl DEPC-treated H$_2$O and incubate it during 10 minutes at 65° C. Subsequently spin it and store at −80° C. during at least 12 hours before proceeding to its quantification.

After extracting the RNA, quantification is performed, and next part of this RNA is transformed into cDNA by means of reverse transcription. This reverse transcription process is carried out with the SuperScript™ III First-Strand Synthesis System.

The SuperScript™ III First-Strand Synthesis System is optimized for synthesizing single-strand cDNA from purified poly A RNA or total RNA. RNA molecules from 100 by to more than 12 kb can be detected by means of this system. The amount of starting total RNA can range from 1 pg to 5 µg of total RNA. The SuperScript™ III Reverse Transcriptase is a version of M-MLV RT that has been improved to reduce the activity of RNase H and to assure greater thermal stability. This enzyme is used to synthesize cDNA in a temperature range of 42-55° C., assuring maximum specificity, obtaining a greater amount of cDNA and more cDNA products with their entire extension in comparison with other reverse transcriptases. Given that the SuperScript™ III Reverse Transcriptase is not inhibited by the presence of ribosomal and transference RNA, it can be used to synthesize single-strand cDNA from preparations of total RNA.

The process to abide by for obtaining cDNA from the RNA extracted by the TRIZOL process is the following:

Up to 5 µg of total RNA together with a mixture of primers and nucleotides are mixed in a PCR cryotube. Specifically, 50 µM (final concentration) Oligo dT primers and 1 µl of 2 µM gene-specific primer and 50 ng/µl of Random Hexamers and the volume of DEPC-treated H$_2$O necessary to reach the final volume of 10 µl are added to the cryotube per microliter of RNA, up to a total of 10 µl.

Incubate at 65° C. for 5 minutes. Once this time has elapsed, leave in ice for at least 1 minute.

Prepare the cDNA synthesis mixture formed by: 2 µl of 10× buffer, 4 µl of 25 mM MgCl$_2$, 2 µl of 0.1 M DTT, 1 µl of RNaseOUT™ (40 U/µl) and 1 µl of SuperScript™ III RT (200 U/µl).

Add 10 µl of the cDNA synthesis mixture to the 10 µl mixture previously made with the RNA and the primers. Mix by spinning and incubate as follows:
Oligo dT or gene-specific primer: 50 minutes at 50° C.
Random hexamers: 10 minutes at 25° C. followed by 50 minutes at 50° C.

Finish the reaction at 85° C. for 5 minutes. After this time has elapsed, cool in ice.

Spin and add 1 µl of RNase H to each tube and incubate during 20 minutes at 37° C.

The synthesized cDNA can be used immediately or can be stored at −20° C.

The kit includes a control RNA: HeLa RNA (10 ng/µl), and primers for amplifying the β-actin gene from this RNA. As control reactions to assure the proper functioning of the kit, the following must be performed:

Dilute the HeLa RNA to 100 pg/µl with DEPC-treated H$_2$O.

Prepare the mixture of RNA and primers in PCR microtubes.

| reagent | +RT Control | −RT Control |
|---|---|---|
| Diluted HeLa RNA | 1 µl | 1 µl |
| Oligo dT | 1 µl | 1 µl |
| 10 mM dNTP mix | 1 µl | 1 µl |
| DEPC-treated H$_2$O | 7 µl | 7 µl |

Incubate the samples at 65° C. for 5 minutes. Once this time has elapsed, incubate in ice for at least 1 minute. Spin and add the following:

| Reagent | +RT Control | −RT Control |
|---|---|---|
| 10X buffer | 2 µl | 2 µl |
| 25 mM MgCl2 | 4 µl | 4 µl |
| 0.1M DTT | 2 µl | 2 µl |
| RNaseOUT ™ (40 U/µl) | 1 µl | 1 µl |
| SuperScript ™III RT (200 U/µl) | 1 µl | 1 µl |
| DEPC-treated H$_2$O | — | 1 µl |

Spin and incubate the samples at 50° C. during 50 minutes.

Finish the reaction at 85° C. for 5 minutes. Once this time has elapsed, cool in ice.

Spin. Add 1 µl of RNase H to each tube and incubate for 20 minutes at 37° C.

Prepare a PCR microtube for each control reaction by adding: 38.1 µl of DEPC-treated H$_2$O, 5 µl of 10× PCR buffer without Mg, 1.5 µl of 50 mM MgCl$_2$, 1 µl of dNTP mix, 1 µl of forward β-actin (10 µM), 1 µl of reverse β-actin (10 µM), 2 µl of cDNA, 0.4 µl of Taq DNA Polymerase (5U/µl), the final volume of the reaction being 50 µl.

Spin and introduce the PCR microtubes in the thermal cycler. Carry out PCR according to the following program: 2 minutes at 94° C. and 40 cycles formed by three 15-second steps at 94° C., 30 seconds at 55° C. and 60 seconds at 72° C.

Once the PCR is finished, keep the microtubes at 4° C.

Analyze 10 µl of each sample by means of agarose gel electrophoresis. A corresponding band should be seen in the +RT control at the height of 353 by of at least 25 ng of the product. No band should be seen in the-RT control.

This cDNA sample allows analyzing gene expression by PCR (Polymerase Chain Reaction) of any gene for which the oligos or specific primers are designed.

The PCR process is described below:

Thaw all the reagents necessary for performing PCR and once thawed, keep them in ice.

Prepare the PCR MIX: (take into account the total number of samples to be amplified+positive control+negative control+1).

| Reagent | 1 reaction (1X) | Final concentration |
|---|---|---|
| H₂O | 39.3 μl | |
| 10X buffer | 5 μl | 1X |
| 100 mM MgCl2 | 1.5 μl | 3 mM |
| 100 mM dNTPs | 1 μl | 200 μM |
| 10 μM F primer | 1 μl | 0.2 μM |
| 10 μM R primer | 1 μl | 0.2 μM |
| cDNA (1:10) | 1 μl | 1:500 |
| Taq polymerase | 0.2 μl | 1 OR |

The PCR program used was the following: 1 2-minute cycle at 94° C. followed by a number of cycles specific for each gene to be amplified, which would consist of the following steps: 30 seconds at 94° C., 30 seconds at the specific annealing temperature of the gene to be amplified, and 60 seconds at 72° C. and a final 10-minute cycle at 72° C.

The result of the amplification of the specific gene by PCR is detected by agarose gel electrophoresis.

Example 6

Protecting the Transport System Against Mechanical Agitation

For the purpose of proving that the agarose-agarase transport mixture system of the present invention provides protection to the transported culture against oscillations and movements during transport, the culture of SK-N-MC cells was subjected to induced mechanical movements for certain time periods: 2, 4, 6 and 8 hours.

Seeding the Cells:

The SK-N-MC cells were seeded in 24-well plates, arranging 200,000 cells in each of the wells, and in their corresponding culture medium.

Adding the Transport Medium on the Cell Culture:

When the culture reached suitable confluence (60-70%, after 2 days), the culture medium of part of the wells is replaced with the agarose plus agarase covering and in the remaining wells, it is replaced with fresh medium without the transport mixture.

Once the transport medium is mixed well and tempered at 37° C., the volume of medium is removed from the wells of the 24-well plate in which the mixture is gradually added, covering the entire cell culture. The medium in the wells in which only the culture medium is to be replaced is also replaced with fresh medium.

Therefore, 1 ml of the mixture is added on the cells seeded in each of the wells and the plate is kept on ice so that the mixture acquires the desired consistency, approximately 15-30 minutes after being added to the plate.

Preparing the Plate for Transport and Transport Conditions:

The plate is then completely sealed with parafilm and is maintained at the transport temperature, 18-23° C., preferably, 22° C., during 24 hours.

Once the 24 hours after preparing the plates have elapsed, the plates are transferred to the agitator and the time of exposure to the movements begins. Before placing the cells in agitation, part of the wells are counted to determine the starting number of cells /well (t=0 h). The cells are maintained in agitation during 2, 4, 6 and 8 hours. After completing these time periods, the corresponding plates are extracted from agitation, and the adhered cells are then lifted off and counted. Then, after the cell count, the degree of adhesion of the cells depending on the presence or not of the agarose plus agarase covering is determined.

FIG. 12 shows the number of cells collected from the wells that contained medium (control) and those that contained the transport mixture (agarose+agarase) during the agitation period (hours). All the counts were done in triplicate.

FIG. 12 shows the number of cells that were maintained adhered to the culture surface during the time in agitation. This figure shows how the number of cells recovered from the wells in which the covering was applied during agitation (agarose+agarase) was greater than that collected from the wells containing only culture medium (without the agarose plus agarase covering) in which the agitation was completed.

These results of this assay prove that the agarose plus agarase covering provides the culture with protection against the mechanical movements and oscillations that may occur during the transport period.

Example 7

Analyzing the Integrity of the Cell Monolayer after the Covering is Removed

The objective of this assay consists of verifying/proving that the integrity of the cell monolayer is not affected after exposure of the culture to the agarose plus agarase mixture and especially that the removal of the covering does not alter the monolayer arrangement of the culture. This assay reinforces the validity of the system in its application as a three-dimensional (3D) culture system.

To that end, the MDCK-II-MDR1 cell line is used. Due to their characteristics and properties, these cells are used as an in vitro model for determining the integrity of the monolayer because they form a strong polarized monolayer in a short time period (2-3 days).

Seeding the Cells:

The MDCK-II-MDR1 cells are seeded in 24-well multi-well transwell plates at a density of 300,000 cells/well. The volume of the well in the basal position is 800 μl, whereas the volume of the well in the apical position (in which the cells were seeded) is 400 μl. The plate is maintained in the incubator at 37° C. and 5% CO₂.

Determining the Formation of the Monolayer:

The day after seeding, the resistance (TEER, in Ω) of the monolayer is determined with the MilliCell RS (Millipore) equipment to start the daily monitoring of the formation of the monolayer; the resistance values are recorded. Then the medium of the wells in both the apical and basal positions is replaced to remove the cells that did not adhere to the culture surface.

The resistance of the monolayer is measured daily to obtain the described values as indicators of the integral monolayer (40-80 Ω×cm²). These values are reached after 2 or 3 days in culture.

Adding the Transport Medium on the Cell Culture:

Once the TEER values which indicate that the monolayer is formed are obtained, the medium of half of the wells of the plate in apical position is replaced with the agarose plus agarase covering to coat the culture. The composition of the transport covering consists of a mixture of 0.5% agarose and 60-80 U/ml of agarose at 1% agarase. When the mixture solidifies, the plate is maintained at 22° C. during 24 hours simulating the transport period.

Preparing the Plate for Transport and Transport Conditions:

The plate is then completely sealed with parafilm and is maintained at the transport temperature, 18-23° C., preferably, 22° C.

Receiving the Plate, Removing the Transport Medium:

After the transport period necessary for reaching its destination, in this case 24 hours of transport have been assayed, the plate must be carefully unwrapped and its surface disinfected with EtOH before being introduced in the cell culture incubator at 37° C. to begin digesting the agarose plus agarase covering and the subsequent verification of the integrity of the monolayer.

Therefore, the plate is introduced in an incubator at 37° C. and 5% $CO_2$. The incubation in these conditions must be for approximately 2 hours. Once the two hours of the first incubation have elapsed, the plate is taken out of the incubator and 400 µl of cell culture medium tempered at 37° C. are added to each of the wells, and the plate is returned to the incubator for another hour.

After the last hour of incubation, the agarose plus agarase covering is removed. The content of the well is mixed very gently and carefully with the aid of a P1000 pipette, and the culture medium mixed with culture medium is carefully removed so as to not entrain and lift the cells which are adhered to the bottom of the well. Tempered fresh medium is then added. At this point, it is necessary to try to remove the maximum amount of medium with agarose, but without risking the culture.

Analyzing the Integrity of the Monolayer after the Agarose Plus Agarase Covering is Removed Once all the wells of the plate are completed, when they all contain fresh medium, the state of the monolayer is verified. To that end, the resistance of the monolayer will first be measured by means of TEER and then the measurement of the passage of 4 KDa Dextran through the cell monolayer is assayed.

TEER Measurement of the Plate after Transport:

The TEER measurement is taken both in the wells in which the agarose plus agarase covering was added during transport and in the wells that were maintained only with culture medium during the entire process.

The resistance values obtained in the wells exposed to the mixture were compared with those obtained in the wells assayed only with medium. They were furthermore compared with the resistance values prior to the arrangement of the agarose plus agarase mixture on part of the culture.

Verifying Cell Cohesion and Integrity of the Monolayer by Means of Analyzing the Passage of Dextran after Transport:

The dextran assay is used to determine the degree of cell cohesion of the culture seeded in the transwell plates, which is a direct indicator of the state of the monolayer. The dextran polymer is bound to fluorescein isocyanate (FITC) molecules, such that it is detected by means of measuring fluorescence. The more integral the cell monolayer is, it will allow a lower passage of the dextran solution and the fluorescence detected in the basal position will be less; in contrast, if the monolayer is not suitably cohered, dextran will more readily traverse it and the fluorescence detected in the basal position will be greater. Therefore, the dextran passage assay was carried after the transport period in both the wells subjected to the transport agarose plus agarase mixture and in the wells not exposed to the covering (only medium).

To carry out the analysis, the culture medium of the wells in the basal position is replaced with 1 ml of fresh medium and the medium of the wells in the apical position is replaced with a dextran solution of 1 mg/ml prepared in culture medium.

After an incubation of 3 hours at 37° C. and in the dark, samples are taken from both the wells in the apical position and in the basal position, and the fluorescence of each of the solutions is suitably measured ($\lambda_{ex}$485, $\lambda_{em}$=538).

The fluorescence values of the wells in the basal position of the cells treated with the agarose plus agarase mixture and the cells cultured only with the culture medium were compared during the analysis.

Once the measurement of the fluorescence of the dextran was taken, the dextran solution contained in the analyzed wells is replaced with fresh medium to allow the culture for 24 more hours and to again analyze the integrity of the monolayer after that period.

Integrity of the Monolayer 24 Hours after the Agarose Plus Agarase Covering is Removed:

24 hours after removing the agarose plus agarase covering, the integrity of the monolayer is again verified to assure that the culture is still stable. This control includes measuring the resistance of the monolayer by means of TEER and analyzing cell cohesion by means of the passage of dextran as done in the previous day after the covering is removed.

FIG. 13a shows the resistance values (TEER) obtained from measuring the control wells that were exposed to the mixture. It shows three different measurements which correspond to the moment prior to adding the agarose plus agarase covering on the culture (prior), the moment immediately after the covering is removed (0 h) and 24 hours after the agarose plus agarase is removed (24 h). The reading was performed in 12 wells for each of the two different conditions; control wells with medium and wells with agarose plus agarase covering.

FIG. 13b shows the percentage of the dextran detected in the wells in basal position, i.e., the percentage of dextran that traversed the cell monolayer. Two readings were performed, the first one corresponding to the moment immediately after the covering is removed (0 h) and the second one 24 hours after the agarose plus agarase mixture is removed (24 h). The analysis was carried out in 12 wells for each of the two different conditions; control wells with medium and wells with agarose plus agarase covering.

From the results obtained as shown in FIGS. 13a and 13b, the TEER values obtained from the wells treated with the mixture and the transport conditions show no difference with respect to those recorded for the control wells in which only culture medium was added.

The percentage of the passage of dextran through the monolayer detected for the wells exposed to the mixture and the transport conditions were unchanged with respect to the percentage detected for the control wells.

The results prove that applying the transport mixture formed by agarose plus agarase does not affect the integrity of the monolayer.

LITERATURE

1—Wang L, Verbruggen G, Almqvist K. F, Elewaut D, Broddelez C, Veys E. M. 2001. "Flow cytometry analysis of the human articular chondrocyte phenotype in vitro". Osteoarthritis and Cartilage, 9: 73-84.

2—Wang L, Almqvist K. F, Broddelez C, Veys E. M, Verbruggen G. 2001. "Evaluation of chondrocyte cell-associated matrix metabolism by flow cytometry". Osteoarthritis and Cartilage, 9: 454-462.

3—Zimrin A. B, Pepper M. S, McMahon G. A, Nguyen F, Montesano, Maciag T. 1996. "An antisense oligonucleotide to the notch ligand jagged enhances fibroblast growth factor-induced angiogenesis in vitro". The Journal of Biological Chemistry, 271(51):32499-502.

4—Ernst M, Oates A, Dunn A. R. 1996. "Gp130-mediated signal transduction in embryonic stem cells involves activation of Jak and Ras/motigen-activated protein kinase pathways". The Journal of Biological Chemistry, 271(47): 30136-43.

5—Laurance M. E, Kwok R. P, Huang M. S, Richards J. P, Lundblad J. R, Goodman R. H. 1997. "Differential activation of viral and cellular promoters by human T-cell lymphotropic virus-1 tax and cAMP-responsive element modulator isoforms". The Journal of Biological Chemistry, 272(5): 2646-51.

6—Yoneda T, Sasaki A, Dunstan C, Williams P. J, Bauss F, Of Clerck Y. A, Mundy G. R. 1997. "Inhibition of osteolytic bone metastasis of breast cancer by combined treatment with the bisphosphonate ibandronat and tissue inhibitor of the matrix metalloproteinase-2" The Journal of Clinical Investigation, 99(10): 2509-17.

7—Kirsc K. H, Georgescu M. M, Ishimaru S, Hanafusa H. 1999. "CMS: an adapter molecule involved in cytoskeletal rearrangements". Proceedings of the National Academy of Sciences of the United States of America, 96(11): 6211-6.

8—Ivankovic-Diki I, Grönroos E, Blaukat A, Barth B. U, Dikic I. 2000. "Pyk2 and FAK regulate neurite outgrowth induced by growth factors and integrins". Nature Cell Biology, 2(9): 574-81.

9—Miller K. A, Chung J, Lo D, Jones J. C, Thimmapaya B, Weitzmen S. A. 2000. "Inhibition of laminin-5 production in breast epithelial cells by overexpression of p300". The Journal of Biological Chemistry, 275(11): 8176-82.

10—Leventhal P. S, Feldman E. L. 1996. "Tyrosine phosphorylation and enhanced expression of paxillin during neuronal differentiation in vitro". The Journal of Biological Chemistry, 271(11): 5957-60.

11—Khademhosseini A, May A, Sefton M. V. 2005. "Conformal coating of mammalian cells immobilized onto magnetically driven beads". Tissue Engineering, 11(11-12): 1797-806.

12—Jones K. S, Sefton M. V, Gorczynski R. M. 2004. "In vivo recognition by the host adaptive immune system of microencapsulated xenogeneic cells". Transplantation, 78(10): 1454-62.

13—Rahforth B, Weisser J, Sternkopf F, Aigner T, von der Mark K, Bräuer R. 1998. "Transplantation of allograft chondrocytes embedded in agarose gel into cartilage defects of rabbits". Osteoarthritis and cartilage, 6(1): 50-65.

14—Ling Y, Rubin J, Deng Y, Huang C, Demirci U, Karp J. M, Khademhosseini A. 2007. "A cell-laden microfluidic hydrogel" Lab on a Chip, 7(6): 756-62.

15—Balgude A. P, Yu X, Szymansky R. V, Bellamkonda R. V. 2001. "Agarose gel stiffness determines ratio of DRG neurite extension in 3D cultures". Biomaterials, 22(10): 1077-84.

1613 in P-W, Wu C-C, Chen C-H, Ho H-O, Chen Y-C, Sep M-T. 2005. "Characterization of cortical neuron outgrowth in two- and three-dimensional culture systems". Journal of Biomedical Materials Research. Part B, Applied Biomaterials, 75(1): 146-57.

17—Mauck R. L, Byers B. A, Yuan X, Tuan R. S. "Regulation of cartilaginous ECM gene transcription by chondrocytes and MSC in 3D culture in response to dynamic loading". Biomechanics and Modelling in Mechanobiology, 6(1-2): 113-25.

18—Martin B. C, Miner. E. J, Wiseman S. L, Klank R. L, Gilbert R. J. 2008. "Agarose and methylcellulose hydrogel blends for nerve regeneration applications". Journal of Neural Engineering, 5(2): 221-31.

19—Luo Y, Shoichet M. S. 2004. "Light-activated immobilization of biomolecules to agarose hydrogels for controlled cellular response". Biomacromolecules, 5(6): 2315-23.

The invention claimed is:

1. A cell transport system characterized in that it comprises a cell support, cells and a homogeneous mixture of agarose and agarase, which assures cell integrity and viability during the transport process.

2. The cell transport system according to claim 1, characterized in that said cells belong to any cell type.

3. The cell transport system according to claim 1, characterized in that said cells are selected from the group of adherent cells, semi-adherent cells and non-adherent cells.

4. The transport system according to claim 1, characterized in that the cells are of an animal origin.

5. The transport system according to claim 1, characterized in that the cells are selected from the group of human, murine, canine, bovine and/or ovine cells.

6. The transport system according to claim 1, characterized in that the cells are selected from the group of nervous cells, cells of the central nervous system, cells of the peripheral nervous system, cells of the dermo-epithelial system, cells of the osteoarticular system, pluripotent embryonic progenitor cells, pluripotent adult progenitor cells, multipotent embryonic progenitor cells, multipotent adult progenitor cells, cells of the hematopoietic system, cells of the immune system and/or cells of the muscle system.

7. The transport system according to claim 6, characterized in that the cells are tumor cells or cell lines established from any of the cell types mentioned before.

8. The transport system according to claim 1, characterized in that the cells are selected from the group of neurons, glial cells, non-glial cells, osteoblasts, osteocytes, osteoclasts, chondroblasts, chondrocytes, fibroblasts, keratinocytes, melanocytes, glandular cells, corneal cells, retinal cells, mesenchymal stem cells, hematopoietic stem cells, embryonic stem cells, epithelial cells, platelets, thymocytes, lymphocytes, monocytes, macrophages, myocytes, hepatocytes, renal cells, urethral cells, cardiomyocytes, myoblasts and/or germ cells.

9. The transport system according to claim 1, characterized in that the cells are genetically modified.

10. The transport system according to claim 1, characterized in that the cells are neurons.

11. The transport system according to claim 1, characterized in that the cells are genetically modified neurons.

12. The cell transport system according to claim 1, characterized in that the cells are cultured in the form of a monolayer to which the agarose and agarase mixture is added.

13. The cell transport system according to claim 12, characterized in that the surface of the cell support optionally includes components of the extracellular matrix that increase the capacity of adherence of the cells to the support, allowing the monolayer cell culture.

14. The transport system according to claim 13, characterized in that said component of the extracellular matrix that increases the capacity of adherence of the cells to the support is poly-L-lysine at a concentration of 10-75 µg/ml.

15. The cell transport system according to claim 14, characterized in that the poly-L-lysine concentration in the cell support is 50-70 µg/ml.

16. The cell transport system according to claim 15, characterized in that the poly-L-lysine concentration in the cell support is 60 µg/ml.

17. A cell transport system comprising cells according to claim 1, characterized in that the cells are cultured in suspension embedded in the agarose and agarase mixture.

18. The cell transport system according to claim 1, characterized in that the cell support has any cell culture format.

19. The cell transport system according to claim 18, characterized in that said format is selected from the group comprising plates, flasks, tubes, culture chambers bottles or transwell-type asymmetric systems (three-dimensional culture).

20. The cell transport system according to claim 1, characterized in that the agarase concentration in the transport medium is between 60 and 90 units per milliliter of 1% agarose.

21. The cell transport system according to claim 20, characterized in that the agarase concentration in the transport medium is 80 units per milliliter of 1% agarose.

22. The transport system according to claim 1, characterized in that the agarose used is low melting point agarose.

23. The transport system according to claim 22, characterized in that the melting point of the agarose is close to 42° C.

24. The cell transport system according to claim 1, characterized in that the final agarose concentration in the transport medium is 0.2 to 0.6%.

25. The cell transport system according to claim 24, characterized in that the final agarose concentration in the transport medium is 0.5%.

26. The cell transport system according to claim 25, characterized in that it comprises a mixture of low melting point agarose at a concentration of 0.5% and agarase at a concentration of 80 units per milliliter of 1% agarose.

27. A transport system comprising an agarose and agarase mixture according to claim 1, characterized in that the agarose and agarase mixture remains in semi-solid state at temperatures of not more than 25° C.

28. The cell transport system according to claim 1, characterized in that the agarose and agarase mixture remains in liquid state when the agarose is digested by the agarase.

29. The cell transport system according to claim 1, characterized in that the agarose and agarase mixture is removed from the cell support leaving the cell culture ready to be used in different applications.

30. The cell transport system according to claim 1, characterized in that it allows extracting the cells from the transport system by means of basic cell culture techniques.

31. The cell transport system according to claim 1, characterized in that it assures cell viability and integrity of at least 85% of the cultured cells.

32. A method for the transport of cells involving preparing the transport system according to claim 1, transporting and recovering the cells.

33. The method for the transport of cells according to claim 32, characterized in that the step of preparing the cell transport system comprises the following steps:
 a. seeding the cell culture:
 b. preparing the agarose and agarase mixture wherein the agarase concentration in the transport medium is between 60 and 90 units per milliliter of 1% agarose;
 c. adding the mixture of step b to the cell culture:
 d. solidifying the agarose and agarase mixture; and
 e. sealing the transport system.

34. The method for the transport of cells according to claim 33, characterized in that step b involves the following steps:
 i. mixing the agarose solution in the culture medium specific for the type of cell culture to be transported at the established concentration wherein the final agarose concentration in the transport medium is 0.2 to 0.6%;
 ii. adding the agarase at the established concentration to the agarose solution of step i; and
 iii. homogenizing the mixture and tempering it to 37° C.

35. The method for the transport of cells according to claim 33, characterized in that step c involves coating the monolayer cultured cells with the mixture of step b prepared according to the following:
 i. mixing the agarose solution in the culture medium specific for the type of cell culture to be transported at the established concentration wherein the final agarose concentration in the transport medium is 0.2 to 0.6%;
 ii. adding the agarase at the established concentration to the agarose solution of step i; and
 iii. homogenizing the mixture and tempering it to 37° C.

36. The method for the transport of cells according to claim 33, characterized in that step c involves the homogenous mixture of the cells in suspension with the mixture of step b prepared according to the following:
 i. mixing the agarose solution in the culture medium specific for the type of cell culture to be transported at the established concentration wherein the final agarose concentration in the transport medium is 0.2 to 0.6%;
 ii. adding the agarase at the established concentration to the agarose solution of step i; and
 iii. homogenizing the mixture and tempering it to 37° C.

37. The method for the transport of cells according to claim 33, characterized in that step d is carried out at a temperature of less than 37° C. in a period of 15-30 minutes.

38. The method for the transport of cells according to claim 32, characterized in that the transport step is carried out at temperatures of not more than 25° C., the transport time being not more than 60 hours.

39. The method for the transport of cells according to claim 38, characterized in that the transport is carried out in a temperature range between 18 and 23° C., the transport time being not more than 48 hours.

40. The method for the transport of cells according to claim 39, characterized in that the transport is carried out at a temperature of 22° C.

41. The method for the transport of cells according to claim 38, characterized in that the viability of the transported cells is at least 85%.

42. The method for the transport of cells according to claim 32, characterized in that the transport is performed inside portable conditioning devices able to maintain the temperature ranges during the suitable time regardless of the room temperature.

43. The method for the transport of cells according to claim 32, characterized in that the recovery of the cells comprises the following steps:
 f. digesting the agarose and agarase mixture;
 g. removing the transport medium and replacing it with culture medium; and
 h. restoring the cell culture.

44. The method for the transport of cells according to claim 43, characterized in that step f comprises the following steps:
 1. incubating the transport system at 37° C. for a time period between 1.5-2 hours;
 2. adding tempered culture medium; and
 3. incubating the system for an additional hour at 37° C.

45. The method for the transport of cells according to claim 44, characterized in that when the cells are in suspension step f comprises an additional step 4 consisting of centrifuging the system at 800-1000 g.

46. The method for the transport of cells according to claim 43, characterized in that restoring the cell culture involves incubation of the cells at 37° C. and 5% $CO_2$.

47. The method for the transport of cells according to claim 43, characterized in that the cells are extracted from the support transporting them.

48. The method for the transport of cells according to claim 43, characterized in that the cells remain in the support transporting them.

* * * * *